US011795229B2

(12) United States Patent
Manley et al.

(10) Patent No.: US 11,795,229 B2
(45) Date of Patent: Oct. 24, 2023

(54) METHODS OF REDUCING SIDE EFFECTS OF ANTI-CD30 ANTIBODY DRUG CONJUGATE THERAPY

(71) Applicant: SEAGEN INC., Bothell, WA (US)

(72) Inventors: Thomas Manley, Bothell, WA (US); Neil Josephson, Seattle, WA (US)

(73) Assignee: SEATTLE GENETICS, INC., Bothell, WA (US)

( * ) Notice: Subject to any disclaimer, the term of this patent is extended or adjusted under 35 U.S.C. 154(b) by 311 days.

(21) Appl. No.: 16/755,403

(22) PCT Filed: Oct. 11, 2018

(86) PCT No.: PCT/US2018/055354
§ 371 (c)(1),
(2) Date: Apr. 10, 2020

(87) PCT Pub. No.: WO2019/075168
PCT Pub. Date: Apr. 18, 2019

(65) Prior Publication Data
US 2021/0221901 A1    Jul. 22, 2021

Related U.S. Application Data

(60) Provisional application No. 62/764,805, filed on Aug. 16, 2018, provisional application No. 62/639,308, (Continued)

(51) Int. Cl.
*A61P 35/02* (2006.01)
*A61K 31/4164* (2006.01)
(Continued)

(52) U.S. Cl.
CPC ...... *C07K 16/2878* (2013.01); *A61K 31/4164* (2013.01); *A61K 31/475* (2013.01);
(Continued)

(58) Field of Classification Search
CPC ............ C07K 16/2878; A61K 47/6849; A61K 47/6867; A61K 47/6889; A61K 47/6803;
(Continued)

(56) References Cited

U.S. PATENT DOCUMENTS 4,474,893 A   10/1984 Reading
4,714,681 A   12/1987 Reading
(Continued)

FOREIGN PATENT DOCUMENTS

WO   1991/00360 A1   1/1991
WO   1992/05793 A1   4/1992
(Continued)

OTHER PUBLICATIONS

Forero-Torres et al. (Leukernia & Lyrnphoma, Apr. 2015, 56 (4): 1151-1153).*

(Continued)

*Primary Examiner* — Yan Xiao
(74) *Attorney, Agent, or Firm* — MARSHALL, GERSTEIN & BORUN LLP

(57) ABSTRACT

The present disclosure, relates, in general to methods for improving adverse events in subjects receiving treatment with an anti-CD30 antibody drug conjugate, optionally also receiving accompanying chemotherapy. Adverse events include peripheral neuropathy and neutropenia.

20 Claims, 13 Drawing Sheets

Specification includes a Sequence Listing.

Related U.S. Application Data filed on Mar. 6, 2018, provisional application No. 62/580,267, filed on Nov. 1, 2017, provisional application No. 62/570,901, filed on Oct. 11, 2017.

(51) Int. Cl.
  *A61K 31/475* (2006.01)
  *A61K 31/704* (2006.01)
  *C07K 16/28* (2006.01)
  *A61K 47/68* (2017.01)
  *A61K 39/00* (2006.01)

(52) U.S. Cl.
  CPC ........ *A61K 31/704* (2013.01); *A61K 47/6849* (2017.08); *A61K 47/6867* (2017.08); *A61K 47/6889* (2017.08); *A61P 35/02* (2018.01); *A61K 2039/505* (2013.01); *A61K 2039/545* (2013.01)

(58) Field of Classification Search
  CPC ........ A61K 2039/505; A61K 2039/545; A61K 31/4164; A61K 31/475; A61K 31/704; A61P 35/02
  USPC ...................................................... 424/133.1
  See application file for complete search history.

(56) References Cited

U.S. PATENT DOCUMENTS

| | | | |
|---|---|---|---|
| 4,925,648 | A | 5/1990 | Hansen et al. |
| 5,573,920 | A | 11/1996 | Randle |
| 5,601,819 | A | 2/1997 | Wong et al. |
| 5,939,598 | A | 8/1999 | Kucherlapati et al. |
| 6,884,869 | B2 | 4/2005 | Senter et al. |
| 9,211,319 | B2 | 12/2015 | Sievers et al. |
| 2006/0074008 | A1 | 4/2006 | Senter et al. |
| 2009/0010945 | A1 | 1/2009 | Alley et al. |

FOREIGN PATENT DOCUMENTS

| | | |
|---|---|---|
| WO | 1992/08802 A1 | 5/1992 |
| WO | 1993/17715 A1 | 9/1993 |

OTHER PUBLICATIONS

Renwick et al. (Biodrugs 2009, 23(3): 175-186).*
Scott, Brentuximab vedotin: a review in CD30-positive hodgkin lymphoma, Drugs, 77:435-445 (2017).
Shenoy et al., Incidence patterns and outcomes for Hodgkin lymphoma patients in the United States, Adv. Hematol., 2011:725219 (2011).
Singapore Application No. 11202003352S, Search Report, dated Oct. 6, 2021.
Spaepen et al., Can positron emission tomography with [(18)F]-fluorodeoxyglucose after first-line treatment distinguish Hodgkin's disease patients who need additional therapy from others in whom additional therapy would mean avoidable toxicity?, Br. J. Haematol., 115:272-8 (2001).
Straus, Improving outcomes with brentuximab vedotin (BV) plus chemotherapy in patients with newly diagnosed advanced stage hodgkin lymphoma, J. Clin. Oncol., 36(15_suppl):7534-7534 (2018).
Torellis et al., ADVANCE and ADAM: two algorithms for the analysis of global similarity between homologous informational sequences, Comput. Appl. Biosci., 10(1):3-5 (1994).
Torres et al., Extended treatment with brentuximab vedotin in patients with relapsed or refractory CD30-positive hematological malignancies, Leuk. Lymphoma., 56(4):1151-1153 (2014).
Tutt et al., Trispecific F(ab')3 derivatives that use cooperative signaling via the TCR/CD3 complex and CD2 to activate and redirect resting cytotoxic T cells, J. Immunol., 147(1):60-69 (1991).
Van De Donk et al., Brentuximab vedotin, Mabs, 4(4):458-465 (2012).
Vehreschild, Prophylaxis of infectious complications with colony-stimulating factors in adult cancer patients undergoing chemotherapy-evidence-based guidelines from the Infectious Diseases Working Party AGIHO of the German Society for Haematology and Medical Oncology (DGHO), Ann. Oncol., 25(9):1709-1718 (2014).
Younes et al., Brentuximab vedotin combined with ABVD or AVD for patients with newly diagnosed Hodgkin's lymphoma: a phase 1, open-label, dose-escalation study, Lancet. Oncol., 14(13):1348-56 (2013).
Aapro et al., EORTC guidelines for the use of granulocyte-colony stimulating factor to reduce the incidence of chemotherapy-induced febrile neutropenia in adult patients with lymphomas and solid tumours, Eur. J. Cancer, 42(15):2433-2453 (2006).
ADCETRIS (Registered) (brentuximab vedotin) EU summary of product characteristics, available at: http://www.ema.europa.eu/docs/en_GB/document_library/EPAR, last accessed (Aug. 10, 2017).
ADCETRIS (Registered) (brentuximab vedotin) US Prescribing Information. Available at: http://www.seattlegenetics.com/application/files/9414/7621/9892/adcetris_USPI.pdf, last accessed (Aug. 10, 2017).
Adecetris, (brentuximab vedotin) for injection, for intravenous use URL at https://www.accessdata.fda.gov/drugsatfda_docs/label/2014/125388_s056s078lbl.pdf (2014).
Altschul et al., Basic local alignment search tool, J. Mol. Biol., 215(3):403-410 (1990).
Altschul et al., Gapped BLAST and PSI-BLAST: a new generation of protein database search programs, Nucleic Acids Res., 25(17):3389-3402 (1997).
Barnes et al., End-of-treatment but not interim PET scan predicts outcome in nonbulky limited-stage Hodgkin's lymphoma, Ann. Oncol., 22:910-5 (2011).
Boehmerle et al., Chemotherapy-induced neuropathy, Nervenartz, 86(2):156-160 (2015).
Borate et al., Treatment of CD30-positive systemic mastocytosis with brentuximab vedotin, Leuk Res., 44:25-31 (2016).
Borchmann et al., Targeted Beacopp Variants in Patients with Newly Diagnosed Advanced Stage Classical Hodgkin Lymphoma: Final Analysis of a Randomized Phase II Study. Presented at the 57th Annual Meeting of the American Society of Hematology, Blood, 126 (2015).
Borchmann et al., Treatment Reduction in Patients with Advanced-Stage Hodgkin Lymphoma and Negative Interim PET: Final Results of the International, Randomized Phase 3 Trial HD18 by the German Hodgkin Study Group, Haematologica., 102:Abstract S150 (2017).
Bowen et al., Functional effects of CD30 on a large granular lymphoma cell line, YT. Inhibition of cytotoxicity, regulation of CD28 and IL-2R, and induction of homotypic aggregation, J. Immunol., 151(11):5896 5906 (1993).
Campo et al., The 2008 WHO classification of lymphoid neoplasms and beyond: evolving concepts and practical applications, Blood, 117(19):5019-32 (2011).
Canellas et al., Chemotherapy of advanced Hodgkin's disease with MOPP, ABVD, or MOPP alternating with ABVD, N. Engl. J. Med., 327:1478-84 (1992).
Canellas et al., How important is bleomycin in the adriamycin + bleomycin + vinblastine + dacarbazine regimen?, J. Clin. Oncol., 22(8):1532-3 (2004).
Carde et al., Eight cycles of ABVD versus four cycles of BEACOPPescalated plus four cycles of BEACOPPbaseline in stage III to IV, International Prognostic Score = 3, High-risk hodgkin lymphoma: First results of the phase III EORTC 20012 Intergroup Trial, J. Clin. Oncol., 34:2028-36 (2016).
Cheson et al., Revised response criteria for malignant lymphoma, J. Clin. Oncol., 25:579-86 (2007).
Connors et al., Brentuximab vedotin plus doxorubicin, vinblastine, dacarbazine (A plus AVD) as frontline therapy demonstrates superior modified progression-free survival versus ABVD in patients with previously untreated stage III or IV hodgkin lymphoma (HL): the phase 3 echelon-1 study, Blood, Am. Soc. Hematology, 130(Suppl. 1):XP009512659, (2017).

(56) References Cited

OTHER PUBLICATIONS

Connors et al., Brentuximab Vedotin with chemotherapy for Stage III or IV Hodgkin's Lymphoma, The New England J. Med. NEJM., 378(4):331-344 (2017).
Connors et al., Five-year follow-up of brentuximab vedotin combined with ABVD or AVD for advanced-stage classical Hodgkin lymphoma, Blood, 30(11):1375-1377 (2017).
Duvic et al., Results of a phase II trial of brentuximab vedotin for CD30+ cutaneous t-cell lymphoma and lymphomatoid papulosis, J. Clin. Oncol., 33(32):3759-3765 (2015).
Engert A, ABVD or BEACOPP for Advanced Hodgkin Lymphoma, J. Clin. Oncol., 34:1167-9 (2016).
Engert et al., Hodgkin's lymphoma in elderly patients: a comprehensive retrospective analysis from the German Hodgkin's Study Group, J. Clin. Oncol., 23:5052-60 (2005).
Engert et al., Reduced-intensity chemotherapy and PETguided radiotherapy in patients with advanced stage Hodgkin's lymphoma (HD15 trial): a randomised, open-label, phase 3 non-inferiority trial, Lancet., 379:1791-9 (2012).
Fauci et al., Ann Arbor Staging System for Hodgkin's Disease. Harrison's Manual of Medicine, 17th ed. New York, NY: McGraw-Hill (2009).
FDA: FDA, adcetris, highlights of prescribing information, Retrieved from the Internet: URL: https://www.accessdata.fda.gov/drugsatfda_docs/label/2014/125388_s056s078lbl.pdf, 4 (2014).
Forero-Torres et al., Prolonged treatment with brentuximabVedotin (SGN-35) in patients with relapsed or refractory hodgkin lymphoma (HL) or systemic anaplastic large cell lymphoma (sALCL), Blood, Am. Soc. Hematology, 118(21):1585-1586 (2011).
Gordon et al., Randomized phase III trial of ABVD versus Stanford V with or without radiation therapy in locally extensive and advanced-stage Hodgkin lymphoma: an intergroup study coordinated by the Eastern Cooperative Oncology Group (E2496), J. Clin. Oncol., 31(6):684-91 (2013).
Gravanis et al., The european medicines agency review of brentuximab vedotin (Adcetris) for the treatment of adult patients with relapsed or refractory CD30+ hodgkin lymphoma or systemic anaplastic large cell lymphoma: summary of the scientific assessment of the committee for medicinal products for human use, The Oncol., 21(1):102-109 (2015).
Hasenclever et al., A prognostic score for advanced Hodgkin's disease. International Prognostic Factors Project on Advanced Hodgkin's Disease, N. Engl. J. Med., 339:1506-14 (1998).
Higgins et al., Using CLUSTAL for multiple sequence alignments, Methods Enzymol., 266:383-402 (1996).
Hsieh et al., Prevalence of neutropenia in the U.S. population: age, sex, smoking status, and ethnic differences, Ann. Intern. Med., 146(7):486-92 (2007).

International Application No. PCT/US18/55354, International Preliminary Report on Patentability, dated Apr. 23, 2020.
International Application No. PCT/US18/55354, International Search Report and Written Opinion, dated Apr. 29, 2019.
Johnson et al., Adapted Treatment Guided by Interim PETCT Scan in Advanced Hodgkin's Lymphoma, N. Engl. J. Med., 374(25):2419-29 (2016).
Kansara et al., Is primary prophylaxis with granulocyte colony stimulating factor (G-CSF) indicated in the treatment of lymphoma?, Transfusion and Apheresis Science, 49(1):51-55 (2013).
Karlin et al., Applications and statistics for multiple high-scoring segments in molecular sequences, Proc. Natl. Acad. Sci. USA, 90(12):5873-5877 (1993).
Karlin et al., Methods for assessing the statistical significance of molecular sequence features by using general scoring schemes, Proc. Natl. Acad. Sci. USA, 87(6):2264-2268 (1990).
Kostelny et al., Formation of a bispecific antibody by the use of leucine zippers, J. Immunol., 148(5):1547-1553 (1992).
Luftner et al., Pegfilgrastim—rational drug design for the management of chemotherapy-induced neutropenia, Oncol. Res. Treatment, 23(11):595-602 (2005).
Martin et al., Bleomycin pulmonary toxicity has a negative impact on the outcome of patients with Hodgkin's lymphoma, J. Clin. Oncol., 23(30):7614-20 (2005).
Matasar et al., Late morbidity and mortality in patients with Hodgkin's lymphoma treated during adulthood, J. Natl. Cancer Inst., 107(4):djv018 (2015).
Meignan et al., Report on the Second International Workshop on interim positron emission tomography in lymphoma held in Menton, France, Apr. 8-9, 2010, Leuk Lymphoma, 51:2171-80 (2010).
Mikles et al., Brentuximab vedotin (SGN-35) in a 3-year-old child with relapsed systemic anaplastic large cell lymphoma, J. Pediatr. Hematol. Oncol., 36(2):e85-87 (2014).
Ng et al., Hodgkin lymphoma: Late effects of treatment and guidelines for surveillance, Semin. Hematol., 53:209-15 (2016).
Oken et al., Toxicity and response criteria of the Eastern Cooperative Oncology Group, Am. J. Clin. Oncol., 5:649-55 (1982).
Pearson et al., Improved tools for biological sequence comparison, Proc. Natl. Acad. Sci. USA, 85(8):2444-8 (1988).
Ramchandren et al., Brentuximab vedotin plus chemotherapy in north american subjects with newly diagnosed stage III or IV hodgkin lymphoma, Clin. Cance Res., 25(6):1718-1726 (2019).
Renwick et al., Use of filgrastim and pegfilgrastim to support delivery of chemotherapy : Twenty Years of Clinical Experience, Biodrugs, 23(3):175-186 (2009).
Schwab et al., Production of a monoclonal antibody specific for Hodgkin and Sternberg-Reed cells of Hodgkin's disease and a subset of normal lymphoid cells, Nature, 299:65-7 (1982).

\* cited by examiner

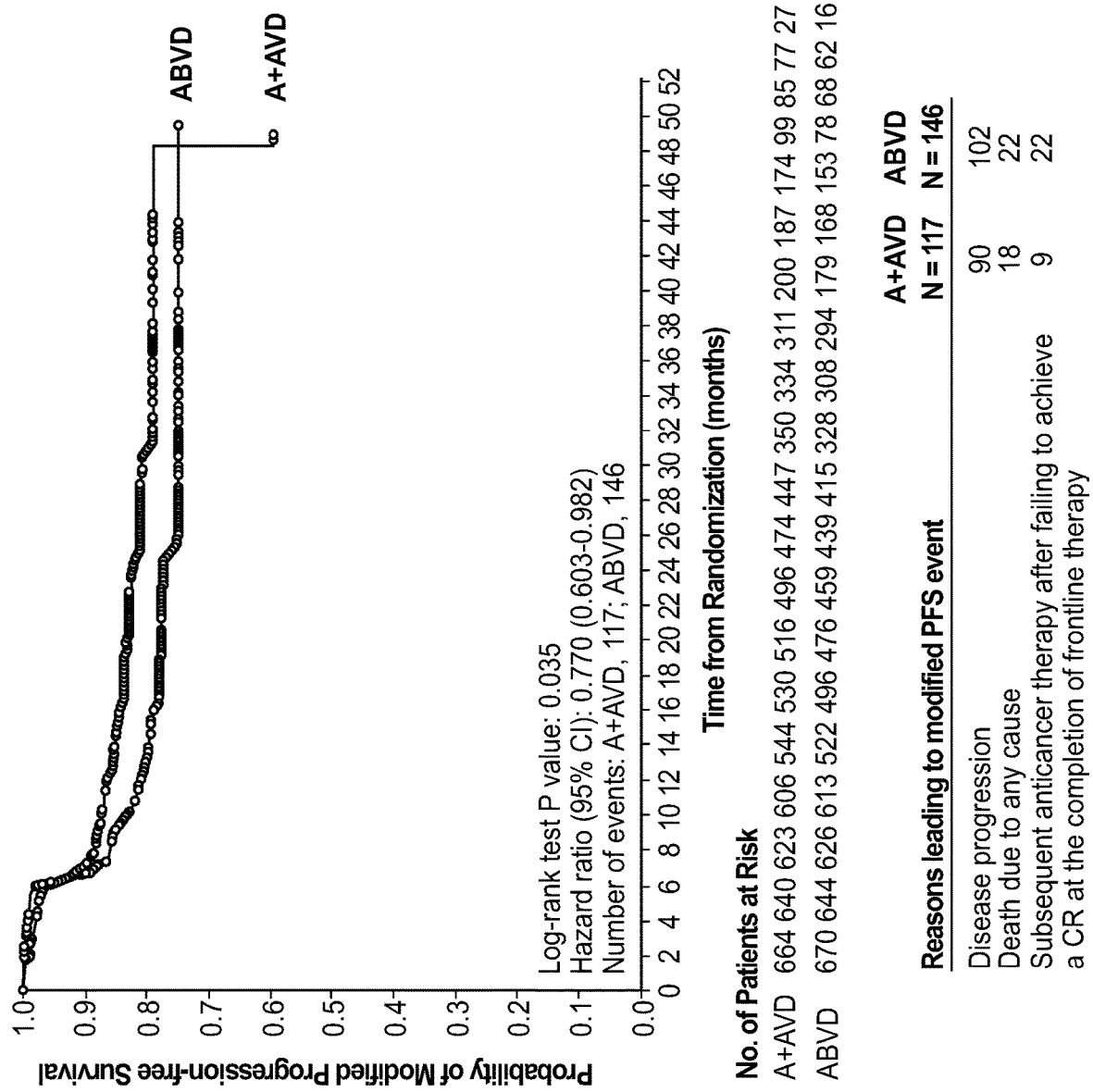

Figure 2

Table 1. Baseline Patient Demographics and Clinical Characteristics (Intent-to-Treat Population).

| Characteristic | A+AVD<br>N = 664 | ABVD<br>N = 670 | Total<br>N = 1334 |
|---|---|---|---|
| Gender — no. (%) | | | |
|   Male | 378 (57) | 398 (59) | 776 (58) |
|   Female | 286 (43) | 272 (41) | 558 (42) |
| Median age (range) — years | 35.0 (18–82) | 37.0 (18–83) | 36.0 (18–83) |
| Age categories (years) — no. (%) | | | |
|   <45 | 451 (68) | 423 (63) | 874 (66) |
|   45–59 | 129 (19) | 145 (22) | 274 (21) |
|   60–64 | 24 (4) | 40 (6) | 64 (5) |
|   ≥65 | 60 (9) | 62 (9) | 122 (9) |
| Race — no. (%) | | | |
|   White | 560 (84) | 554 (83) | 1114 (84) |
|   Asian | 56 (8) | 57 (9) | 113 (8) |
|   Black or African American | 20 (3) | 25 (4) | 45 (3) |
|   Other | 18 (3) | 17 (3) | 35 (3) |
|   Not reported | 10 (2) | 17 (3) | 27 (2) |
| Region — no. (%) | | | |
|   Americas | 261 (39) | 262 (39) | 523 (39) |
|   Europe | 333 (50) | 336 (50) | 669 (50) |
|   Asia | 70 (11) | 72 (11) | 142 (11) |
| Ann Arbor stage at initial diagnosis — no. (%) | | | |
|   Stage I | 0 | 0 | 0 |
|   Stage II* | 1 (<1) | 0 | 1 (<1) |
|   Stage III | 237 (36) | 246 (37) | 483 (36) |
|   Stage IV | 425 (64) | 421 (63) | 846 (64) |
|   Not applicable/unknown/missing | 1 (<1) | 3 (<1) | 4 (<1) |
| IPS — no. (%) | | | |
|   0–1 | 141 (21) | 141 (21) | 282 (21) |
|   2–3 | 354 (53) | 351 (52) | 705 (53) |
|   4–7 | 169 (25) | 178 (27) | 347 (26) |
| ECOG performance status — no. (%) | | | |
|   0 | 376 (57) | 378 (57) | 754 (57) |
|   1 | 259 (39) | 262 (39) | 521 (39) |
|   2 | 28 (4) | 26 (4) | 54 (4) |
|   3 or 4 | 0 | 0 | 0 |
|   Not done/missing | 1 (<1) | 4 (<1) | 5 (<1) |
| Bone marrow involvement at diagnosis or study entry — no. (%) | | | |
|   Yes | 147 (22) | 151 (23) | 298 (22) |
|   No | 502 (76) | 509 (76) | 1011 (76) |
|   Unknown/missing | 15 (2) | 10 (1) | 25 (2) |
| Extranodal involvement at diagnosis — no. (%) | | | |
|   Yes | 411 (62) | 416 (62) | 827 (62) |
|   1 extranodal site | 217 (33) | 223 (33) | 440 (33) |
|   >1 extranodal sites | 194 (29) | 193 (29) | 387 (29) |
|   No | 217 (33) | 228 (34) | 445 (33) |
|   Unknown/missing | 36 (5) | 26 (4) | 62 (5) |
| Patients with any B symptom — no. (%) | 399 (60) | 381 (57) | 780 (58) |

*Patients in this category have major protocol violation.
A+AVD, brentuximab vedotin plus doxorubicin, vinblastine, dacarbazine; ABVD, doxorubicin, bleomycin, vinblastine, dacarbazine; ECOG, Eastern Cooperative Oncology Group; IPS, International Prognostic Score.

Figure 3

Table 2. Summary of Subsequent Therapy and End-of-treatment Deauville Scores for Events Noted in Modified Progression-free Survival per Independent Review Facility and Correlation with Events Noted by Trial Investigators (Intent-to-treat Population).

|  | A+AVD<br>N = 664 | ABVD<br>N = 670 | Total<br>N = 1334 |
|---|---|---|---|
| Patients with modified PFS events per IRF – overall, no. (%) | 117 (100) | 146 (100) | 263 (100) |
| Progression | 90 (77) | 102 (70) | 192 (73) |
| Death | 18 (15) | 22 (15) | 40 (15) |
| PET-positive and subsequent treatment | 9 (8) | 22 (15) | 31 (12) |
| Salvage chemotherapy* | 7/9 (78) | 15/22 (68) | 22/31 (71) |
| Met criteria for: | | | |
| PFS event or modified event per investigator | 7 (100) | 15 (100) | 22 (100) |
| PFS event per investigator | 7/7 (100) | 13/15 (87) | 20/22 (91) |
| PFS event per IRF | 2/7 (29) | 3/15 (20) | 5/22 (23) |
| Deauville score at end of treatment | | | |
| 1 | 0 | 0 | 0 |
| 2 | 0 | 0 | 0 |
| 3 | 0 | 2/15 (13) | 2/22 (9) |
| 4 | 3/7 (43) | 4/15 (27) | 7/22 (32) |
| 5 | 4/7 (57) | 9/15 (60) | 13/22 (59) |
| Radiation | 2/9 (22) | 7/22 (32) | 9/31 (29) |
| Met criteria for: | | | |
| PFS event or modified event per investigator | 2/2 (100) | 7/7 (100) | 9/9 (100) |
| PFS event per investigator | 0 | 1/7 (14) | 1/9 (11) |
| PFS event per IRF | 0 | 1/7 (14) | 1/9 (11) |
| Deauville score at end of treatment | | | |
| 1 | 0 | 0 | 0 |
| 2 | 0 | 0 | 0 |
| 3 | 2/2 (100) | 3/7 (43) | 5/9 (56) |
| 4 | 0 | 3/7 (43) | 3/9 (33) |
| 5 | 0 | 1/7 (14) | 1/9 (11) |

*Salvage chemotherapy included terms 'chemotherapy', 'high-dose chemotherapy plus transplant', and 'immunotherapy' in Standardized Medication Name Group.
A+AVD, brentuximab vedotin plus doxorubicin, vinblastine, dacarbazine; ABVD, doxorubicin, bleomycin, vinblastine, dacarbazine; IRF, independent review facility; PET, positron-emission tomography; PFS, progression-free survival.

Figure 4

Table 3. Summary of Response in the Intent-to-Treat Population.

| Patients with event — no. (%) | A+AVD N = 664 | ABVD N = 670 | p-value | Difference, % (exact 95% CI) |
|---|---|---|---|---|
| Complete remission rate at end of randomized regimen* | 488 (73) | 472 (70) | 0.224 | 3.0 (-2.3–8.4) |
| Overall remission rate at end of randomized regimen[†] | 569 (86) | 553 (83) | 0.116 | 3.2 (-2.2–8.6) |
| Complete remission rate at end of frontline therapy[‡] | 488 (73) | 474 (71) | 0.273 | 2.7 (-2.6–8.1) |
| Deauville score ≤3 after completion of frontline therapy | 570 (86) | 551 (82) | 0.071 | 3.6 (-1.8–9.0) |
| Deauville score ≤2 after completion of frontline therapy | 563 (85) | 537 (80) | 0.025 | 4.6 (-0.8–10.0) |
| PET negativity (Deauville 1–3) at Cycle 2 | 588 (89) | 577 (86) | 0.181 | 2.4 (-2.9–7.8) |
| Summary of Deauville score at Cycle 2 | | | | |
| 1 | 435 (66) | 414 (62) | | |
| 2 | 131 (20) | 133 (20) | | |
| 3 | 22 (3) | 30 (4) | | |
| 4 | 26 (4) | 28 (4) | | |
| 5 | 21 (3) | 30 (4) | | |

*Defined as the proportion of patients who achieve complete remission[20] at the end of treatment with the randomized regimen (A+AVD or ABVD).
[†]Defined as the proportion of patients who achieve complete or partial remission[20] at the end of treatment with the randomized regimen (A+AVD or ABVD).
[‡]Defined as the proportion of patients who achieve complete remission after completion of either the randomized regimen (A+AVD or ABVD) or alternate frontline therapy.
A+AVD, brentuximab vedotin plus doxorubicin, vinblastine, dacarbazine; ABVD, doxorubicin, bleomycin, vinblastine, dacarbazine; CI, confidence interval; PET, positron emission tomography.

Figure 5

Table 4. Summary of Adverse Events in the Safety Population.

| Safety summary — no. (%) | A+AVD<br>N = 662 | | ABVD<br>N = 659 | |
|---|---|---|---|---|
| Any adverse event | 653 (99) | | 646 (98) | |
| Drug-related adverse event | 641 (97) | | 617 (94) | |
| Grade ≥3 adverse event | 549 (83) | | 434 (66) | |
| Drug-related Grade ≥3 adverse event | 525 (79) | | 389 (59) | |
| Serious adverse event | 284 (43) | | 178 (27) | |
| Drug-related serious adverse event | 240 (36) | | 125 (19) | |
| Adverse events resulting in drug or dose discontinuation | 88 (13) | | 105 (16) | |
| Adverse event resulting in dose modification | 423 (64) | | 293 (44) | |
|     Dose held | 44 (7) | | 32 (5) | |
|     Dose interrupted | 22 (3) | | 33 (5) | |
|     Dose reduced | 191 (29) | | 65 (10) | |
|     Dose delayed | 318 (48) | | 217 (33) | |
| On-study deaths* | 9 (1) | | 13 (2) | |
| Deaths due to drug-related adverse events | 8 (1) | | 7 (1) | |
| Rate of hospitalization — per patient-year (95% CI) | 0.3363 (0.31–0.37) | | 0.2277 (0.20–0.25) | |
| Common adverse events — no. (%) | Any grade | Grade ≥3 | Any grade | Grade ≥3 |
|     Neutropenia | 382 (58) | 357 (54) | 295 (45) | 260 (39) |
|     Nausea | 348 (53) | 20 (3) | 371 (56) | 7 (1) |
|     Constipation | 279 (42) | 11 (2) | 241 (37) | 4 (<1) |
|     Vomiting | 216 (33) | 23 (3) | 183 (28) | 9 (1) |
|     Fatigue | 211 (32) | 19 (3) | 211 (32) | 7 (1) |
|     Peripheral sensory neuropathy | 189 (29) | 31 (5) | 111 (17) | 3 (<1) |
|     Diarrhea | 181 (27) | 19 (3) | 121 (18) | 5 (<1) |
|     Pyrexia | 179 (27) | 19 (3) | 147 (22) | 13 (2) |
|     Neuropathy peripheral | 174 (26) | 27 (4) | 85 (13) | 6 (<1) |
|     Alopecia | 173 (26) | 1 (<1) | 146 (22) | 0 |
|     Weight decreased | 148 (22) | 6 (<1) | 40 (6) | 1 (<1) |
|     Abdominal pain | 142 (21) | 21 (3) | 65 (10) | 4 (<1) |
|     Anemia | 140 (21) | 54 (8) | 67 (10) | 25 (4) |
|     Stomatitis | 138 (21) | 10 (2) | 104 (16) | 3 (<1) |
|     Febrile neutropenia | 128 (19) | 128 (19) | 52 (8) | 52 (8) |
|     Bone pain | 126 (19) | 6 (<1) | 66 (10) | 1 (<1) |
|     Insomnia | 126 (19) | 4 (<1) | 82 (12) | 1 (<1) |
|     Decreased appetite | 118 (18) | 5 (<1) | 76 (12) | 2 (<1) |
|     Cough | 97 (15) | 0 | 123 (19) | 0 |
|     Headache | 95 (14) | 2 (<1) | 94 (14) | 2 (<1) |
|     Arthralgia | 89 (13) | 2 (<1) | 78 (12) | 0 |
|     Neutrophil count decreased | 86 (13) | 83 (13) | 79 (12) | 67 (10) |
|     Dyspepsia | 84 (13) | 1 (<1) | 75 (11) | 0 |
|     Paresthesia | 84 (13) | 0 | 73 (11) | 0 |
|     Back pain | 83 (13) | 4 (<1) | 49 (7) | 0 |
|     Dyspnea | 82 (12) | 9 (1) | 124 (19) | 11 (2) |
|     Myalgia | 81 (12) | 3 (<1) | 71 (11) | 3 (<1) |
|     Pain in extremity | 81 (12) | 2 (<1) | 67 (10) | 1 (<1) |
|     Oropharyngeal pain | 72 (11) | 2 (<1) | 55 (8) | 3 (<1) |
|     Upper respiratory tract infection | 70 (11) | 5 (<1) | 70 (11) | 3 (<1) |
|     Alanine aminotransferase increased | 68 (10) | 22 (3) | 26 (4) | 1 (<1) |

| Primary prophylaxis with G-CSF— no. (%) | No G-CSF primary prophylaxis (n = 579) | G-CSF primary prophylaxis (n = 83) | No G-CSF primary prophylaxis (n = 616) | G-CSF primary prophylaxis (n = 43) |
|---|---|---|---|---|
| Febrile neutropenia in Cycle 1 | 61 (11) | 1 (1) | 24 (4) | 2 (5) |
| Febrile neutropenia on study | 119 (21) | 9 (11) | 49 (8) | 3 (7) |
| Neutropenia† | 425 (73) | 29 (35) | 352 (57) | 9 (21) |
| Grade ≥3 neutropenia† | 406 (70) | 24 (29) | 309 (50) | 8 (19) |
| Grade ≥3 adverse event† | 502 (87) | 47 (57) | 414 (67) | 20 (47) |
| Infections and infestations (SOC) | 322 (56) | 39 (47) | 312 (51) | 19 (44) |
| Grade ≥3 infections and infestations (SOC) | 107 (18) | 9 (11) | 63 (10) | 3 (7) |
| Serious adverse event | 257 (44) | 27 (33) | 171 (28) | 7 (16) |
| Serious adverse events of febrile neutropenia, neutropenia, sepsis, neutropenic sepsis, pyrexia, or infections and infestations (SOC) | 190 (33) | 20 (24) | 107 (17) | 4 (9) |
| On-study deaths* | 8 (1) | 1 (1)‡ | 12 (2) | 1 (2) |

*Defined as deaths that occur within 30 days of the last dose of frontline therapy. †Includes preferred terms of 'neutropenia' and 'neutrophil count decreased'. ‡The patient in the A+AVD arm who had G-CSF primary prophylaxis received G-CSF for treatment of neutropenia, which occurred prior to Day 5. A+AVD, brentuximab vedotin plus doxorubicin, vinblastine, dacarbazine; ABVD, doxorubicin, bleomycin, vinblastine, dacarbazine; CI, confidence interval; G-CSF, granulocyte colony-stimulating factor; SOC, system organ class

Details of Brentuximab Vedotin Dose Modifications.

| Toxicity | ≤Grade 2 | | ≥Grade 3 | |
|---|---|---|---|---|
| Non-hematological (excluding neuropathy) | Continue at same dose level | | Hold A+AVD dosing until toxicity has resolved to ≤Grade 2 or has returned to baseline* | |
| Hematological | Continue at same dose level | | For neutropenia, manage with growth factors (G-CSF or GM-CSF) per institutional guidelines. For thrombocytopenia, consider platelet transfusion and/or proceed according to institutional guidelines. For anemia, manage per institutional guidelines | |
| Peripheral neuropathy | Grade 1 Continue at same dose level | Grade 2 Reduce dose to 0.9 mg/kg and resume treatment; if already at 0.9 mg/kg, continue dosing at that level | Grade 3 Withhold brentuximab vedotin until toxicity is ≤Grade 2, then reduce dose to 0.9 mg/kg and resume treatment. If already at 0.9 mg/kg, consult with sponsor (AVD may be continued or held concurrently at physician's discretion) | Grade 4 Discontinue brentuximab vedotin |

*Patients who develop clinically insignificant Grade 3 or 4 electrolyte laboratory abnormalities may continue study treatment without interruption.
A+AVD, brentuximab vedotin plus doxorubicin, vinblastine, dacarbazine; G-CSF, granulocyte colony-stimulating factor; GM-CSF, granulocyte-macrophage colony-stimulating factor.

Figure 8

Summary of First Subsequent Chemotherapy for Patients Failing to Achieve a Complete Response at the Completion of Frontline Therapy.

| First subsequent chemotherapy — no. (%) | A+AVD<br>N = 9 | ABVD<br>N = 22 | Total<br>N = 31 |
|---|---|---|---|
| Overall | 7 (78) | 15 (68) | 22 (71) |
| Cisplatin + cytarabine + dexamethasone | 3 (33) | 3 (14) | 6 (19) |
| Carboplatin + etoposide + ifosfamide | 2 (22) | 2 (9) | 4 (13) |
| Cisplatin + cytarabine + etoposide + methylprednisolone | 1 (11) | 3 (14) | 4 (13) |
| Brentuximab vedotin | 0 | 1 (5) | 1 (3) |
| Brentuximab vedotin + bendamustine + ASCT | 0 | 1 (5) | 1 (3) |
| Carboplatin + etoposide + ifosfamide + ASCT | 1 (11) | 0 | 1 (3) |
| Carboplatin + etoposide + ifosfamide + rituximab + ASCT | 0 | 1 (5) | 1 (3) |
| Carboplatin + etoposide + ifosfamide + SCT | 0 | 1 (5) | 1 (3) |
| Dexamethasone + cisplatin + gemcitabine | 0 | 1 (5) | 1 (3) |
| Dexamethasone + cytarabine + procarbazine | 0 | 1 (5) | 1 (3) |
| Rituximab + bendamustine | 0 | 1 (5) | 1 (3) |

A+AVD, brentuximab vedotin plus doxorubicin, vinblastine, dacarbazine; ABVD, doxorubicin, bleomycin, vinblastine, dacarbazine; ASCT, autologous stem cell transplant; SCT, stem cell transplant.

Figure 9

Summary of Reasons for Switching to Alternative Chemotherapy during Frontline Therapy (Safety Population).

| Reason for switching to alternative chemotherapy — no. (%) | A+AVD<br>N = 662 | ABVD<br>N = 659 | Total<br>N = 1321 |
|---|---|---|---|
| Adverse event | 12 (80) | 1 (11) | 13 (54) |
| Deauville score assessment of 5 | 1 (7) | 4 (44) | 5 (21) |
| Other | 2 (13)* | 4 (44)† | 6 (25) |

A+AVD, brentuximab vedotin plus doxorubicin, vinblastine, dacarbazine; ABVD, doxorubicin, bleomycin, vinblastine, dacarbazine.
*Reason was unspecified for both patients
†Reasons included toxicity (1), unsatisfactory response (3)

Figure 10

| | A+AVD N = 662 | | | |
|---|---|---|---|---|
| | Brentuximab vedotin | Doxorubicin | Vinblastine | Dacarbazine |
| Duration of treatment (weeks) | | | | |
| n | 662 | 656 | 661 | 661 |
| Mean (standard deviation) | 23.19 (5.646) | 23.88 (5.362) | 23.60 (5.600) | 23.89 (5.335) |
| Median | 24.21 | 24.57 | 24.43 | 24.57 |
| Min, max | 2.0, 35.0 | 2.0, 48.9 | 2.0, 48.9 | 2.0, 48.9 |
| Total number of doses received | | | | |
| n | 662 | 656 | 661 | 661 |
| Mean (standard deviation) | 10.8 (2.60) | 11.2 (2.38) | 11.0 (2.50) | 11.2 (2.37) |
| Median | 12.0 | 12.0 | 12.0 | 12.0 |
| Min, max | 1, 12 | 1, 12 | 1, 12 | 1,12 |
| Number of treated cycles | | | | |
| n | 662 | 656 | 661 | 661 |
| Mean (standard deviation) | 5.5 (1.21) | 5.6 (1.13) | 5.6 (1.18) | 5.6 (1.12) |
| Median | 6.0 | 6.0 | 6.0 | 6.0 |
| Min, max | 1, 6 | 1, 6 | 1, 6 | 1, 6 |
| Action on study drug— no. (%) | 434 (66) | 355 (54) | 378 (57) | 350 (53) |
| Dose reduced prescribed | 170 (26) | 25 (4) | 58 (9) | 29 (4) |
| Dose reduced non-prescribed | 3 (<1) | 2 (<1) | 1 (<1) | 2 (<1) |
| Dose increased prescribed | 0 | 0 | 0 | 0 |
| Dose increased non-prescribed | 0 | 0 | 0 | 0 |
| Dose held | 41 (6) | 2 (<1) | 12 (2) | 1 (<1) |
| Dose missed | 0 | 0 | 1 (<1) | 0 |
| Dose interrupted | 12 (2) | 8 (1) | 1 (<1) | 11 (2) |
| Dose delayed | 315 (48) | 323 (49) | 319 (48) | 317 (48) |
| Dose discontinued permanently | 71 (11) | 38 (6) | 52 (8) | 38 (6) |
| | ABVD N = 659 | | | |
| | Bleomycin | Doxorubicin | Vinblastine | Dacarbazine |
| Duration of treatment (weeks) | | | | |
| n | 659 | 649 | 659 | 659 |
| Mean (standard deviation) | 22.38 (5.694) | 23.88 (4.669) | 23.65 (4.880) | 23.86 (4.658) |
| Median | 24.00 | 24.00 | 24.00 | 24.00 |
| Min, max | 2.0, 39.1 | 2.0, 45.4 | 2.0, 45.4 | 2.0, 45.4 |
| Total number of doses received | | | | |
| n | 659 | 649 | 659 | 659 |
| Mean (standard deviation) | 10.7 (2.64) | 11.4 (2.00) | 11.3 (2.13) | 11.4 (2.02) |
| Median | 12.0 | 12.0 | 12.0 | 12.0 |
| Min, max | 1, 12 | 1, 12 | 1, 12 | 1, 12 |
| Number of treated cycles | | | | |
| n | 659 | 649 | 659 | 659 |
| Mean (standard deviation) | 5.4 (1.24) | 5.7 (0.95) | 5.7 (1.01) | 5.7 (0.96) |
| Median | 6.0 | 6.0 | 6.0 | 6.0 |
| Min, max | 1, 6 | 1, 6 | 1, 6 | 1, 6 |
| Action on study drug— no. (%) | 315 (48) | 250 (38) | 281 (43) | 256 (39) |
| Dose reduced prescribed | 17 (3) | 24 (4) | 61 (9) | 19 (3) |
| Dose reduced non-prescribed | 1 (<1) | 1 (<1) | 2 (<1) | 3 (<1) |
| Dose increased prescribed | 0 | 0 | 1 (<1) | 0 |
| Dose increased non-prescribed | 1 (<1) | 1 (<1) | 0 | 1 (<1) |
| Dose held | 32 (5) | 1 (<1) | 9 (1) | 1 (<1) |
| Dose missed | 2 (<1) | 2 (<1) | 3 (<1) | 2 (<1) |
| Dose interrupted | 6 (<1) | 11 (2) | 3 (<1) | 28 (4) |
| Dose delayed | 211 (32) | 218 (33) | 219 (33) | 215 (33) |
| Dose discontinued permanently | 106 (16) | 22 (3) | 34 (5) | 22 (3) |

A+AVD, brentuximab vedotin plus doxorubicin, vinblastine, dacarbazine; ABVD, doxorubicin, bleomycin, vinblastine, dacarbazine.

Figure 11

Summary of Peripheral Neuropathy (SMQ) (Safety Population).

| Patients with event — no. (%) | A+AVD<br>N = 662 | ABVD<br>N = 659 | Total<br>N = 1321 |
|---|---|---|---|
| Any peripheral neuropathy (SMQ) event | 442 (67) | 286 (43) | 728 (55) |
| Peripheral motor neuropathy (SSQ)* | 74 (11) | 29 (4) | 103 (8) |
| Peripheral motor neuropathy | 42 (6) | 8 (1) | 50 (4) |
| Muscular weakness | 36 (5) | 18 (3) | 54 (4) |
| Autonomic neuropathy | 1 (<1) | 2 (<1) | 3 (<1) |
| Peroneal nerve palsy | 1 (<1) | 2 (<1) | 3 (<1) |
| Muscle atrophy | 2 (<1) | 0 | 2 (<1) |
| Hypotonia | 0 | 1 (<1) | 1 (<1) |
| Peripheral sensory neuropathy (SSQ)† | 429 (65) | 273 (41) | 702 (53) |
| Peripheral sensory neuropathy | 189 (29) | 111 (17) | 300 (23) |
| Neuropathy peripheral | 174 (26) | 85 (13) | 259 (20) |
| Paraesthesia | 84 (13) | 73 (11) | 157 (12) |
| Hypoaesthesia | 33 (5) | 27 (4) | 60 (5) |
| Polyneuropathy | 10 (2) | 6 (<1) | 16 (1) |
| Neuralgia | 8 (1) | 1 (<1) | 9 (<1) |
| Burning sensation | 2 (<1) | 4 (<1) | 6 (<1) |
| Dysaesthesia | 4 (<1) | 1 (<1) | 5 (<1) |
| Gait disturbance | 3 (<1) | 0 | 3 (<1) |
| Toxic neuropathy | 3 (<1) | 0 | 3 (<1) |
| Neurotoxicity | 2 (<1) | 0 | 2 (<1) |
| Sensory disturbance | 0 | 1 (<1) | 1 (<1) |

*Includes the preferred term of peripheral motor neuropathy, peripheral sensorimotor neuropathy, peroneal nerve palsy, muscular weakness, hypotonia, or muscle atrophy.
†Includes all other preferred terms except for autonomic neuropathy, and the six preferred terms for peripheral motor neuropathy.
A+AVD, brentuximab vedotin plus doxorubicin, vinblastine, dacarbazine; ABVD, doxorubicin, bleomycin, vinblastine, dacarbazine; SMQ, standardized Medical Dictionary for Regulatory Activities query; SSQ, special search query.

METHODS OF REDUCING SIDE EFFECTS OF ANTI-CD30 ANTIBODY DRUG CONJUGATE THERAPY

CROSS REFERENCE TO RELATED APPLICATIONS

The present application claims the priority benefit of U.S. Provisional patent Application No. 62/570,901, filed Oct. 11, 2017, U.S. Provisional Patent Application No. 62/580,267, filed Nov. 1, 2017, U.S. Provisional Patent Application No. 62/639,308, filed Mar. 6, 2018, and U.S. Provisional Patent Application No. 62/764,805, filed Aug. 16, 2018, each of which is incorporated herein by reference.

FIELD OF THE DISCLOSURE

The present disclosure relates, in general, to methods of reducing neutropenia and peripheral neuropathy in subjects receiving anti-CD30 antibody drug conjugate therapy, optionally in combination with a chemotherapeutic regimen of doxorubicin, vinblastine, and dacarbazine.

BACKGROUND

Outcomes for patients with advanced-stage Hodgkin lymphoma have improved dramatically over the past half century.[1] Although regional differences exist, the most commonly used frontline regimen, ABVD (doxorubicin, bleomycin, vinblastine, and dacarbazine), has not been modified since its original description in 1975.

Up to 30% of patients with stage III/IV Hodgkin lymphoma harbor refractory disease or relapse following frontline ABVD.[2-4] Bleomycin, considered to have the least activity of the four components of ABVD, is associated with unpredictable and sometimes fatal pulmonary toxicity, and is often dropped from later cycles of chemotherapy due to pulmonary symptoms.[5,6] Recent studies suggest that response-adapted therapy guided by interim positron-emission tomography (PET) with 18F-fluorodeoxyglucose can provide a more individualized treatment approach in which treatment intensity is de-escalated/intensified depending on the early response to treatment.[7,8] Efforts are also being made to incorporate new drugs into established backbones to improve efficacy and reduce toxicity.[9]

CD30 is a characteristic surface antigen expressed on the Reed-Sternberg cells of classical Hodgkin lymphoma.[10] Brentuximab vedotin is an antibody-drug conjugate composed of an anti-CD30 monoclonal antibody conjugated by a protease-cleavable linker to the microtubule disrupting agent, monomethyl auristatin E. Brentuximab vedotin has been approved for the treatment of classical Hodgkin lymphoma patients after failure of autologous stem cell transplant (ASCT) or after failure of at least 2 prior multi-agent chemotherapy regimens in patients who are not ASCT candidates, and as consolidation post-ASCT for Hodgkin lymphoma patients at increased risk of relapse/progression.[11,12] It has also been approved for systemic anaplastic large cell lymphoma after failure of at least one prior multi-agent chemotherapy regimen.

A previous phase 1, dose-escalation study in advanced Hodgkin lymphoma evaluated frontline brentuximab vedotin combined with either ABVD or AVD (doxorubicin, vinblastine, dacarbazine) [Younes A, Connors J M, Park S I, et al. Brentuximab vedotin combined with ABVD or AVD for patients with newly diagnosed Hodgkin's lymphoma: a phase 1, open-label, dose-escalation study. Lancet Oncol 2013; 14:1348-56].

SUMMARY

The present disclosure provides improved methods for administering an anti-CD30 antibody-drug conjugate and reducing adverse events in a subject receiving anti-CD30 antibody drug conjugate therapy. In some embodiments, side effects such as peripheral neuropathy are reduced by adjusting the amount and/or timing of anti-CD30 antibody drug conjugate. In other embodiments, side effects including neutropenia, febrile neutropenia or infection are reduced by co-administration of the anti-CD30 antibody drug conjugate with a granulopoiesis stimulating factor.

In one aspect, the disclosure provides a method of administering an anti-CD30 drug conjugate, e.g., brentuximab vedotin, to a subject in need thereof at a dose of 0.9 mg/kg, administered, e.g., every two weeks. The subject in need thereof may have a hematologic cancer, for example, classical Hodgkin's lymphoma. In various embodiments, the disclosure provides a method for treating a subject that has exhibited Grade 2 or greater peripheral neuropathy after starting anti-CD30 antibody drug conjugate therapy at a dose of 1.2 mg/kg or more, comprising administering anti-CD30 antibody drug conjugate at a dose of 0.9 mg/kg. In various embodiments, the subject exhibits Grade 2 or Grade 3 peripheral neuropathy. In various embodiments, when the subject exhibits Grade 3 neuropathy, the administration of anti-CD30 antibody drug conjugate is withheld until peripheral neuropathy decreases to Grade 2 or less and then 0.9 mg/kg anti-CD30 antibody drug conjugate is administered.

In various embodiments, when the subject exhibits Grade 3 neuropathy, the administration of anti-CD30 antibody drug conjugate is reduced, e.g., to 0.9 mg/kg, until peripheral neuropathy decreases to Grade 2 or less and then 0.9 mg/kg anti-CD30 antibody drug conjugate is administered or maintained.

In various embodiments, the subject exhibited Grade 2 or 3 peripheral neuropathy after starting brentuximab vedotin administration at a dose of 1.8 mg/kg every three weeks.

In various embodiments, the subject exhibited Grade 2 or 3 peripheral neuropathy after starting anti-CD30 antibody drug conjugate therapy at a dose of 1.2 mg/kg every two weeks, optionally in combination with a chemotherapeutic regimen. It is contemplated that the therapeutic regimen may include chemotherapeutics known in the field of cancer treatment. Exemplary chemotherapeutics are disclosed in greater detail in the Detailed Description. In various embodiments, the methods herein include treatment comprising a chemotherapy consisting essentially of doxorubicin (A), vinblastine (V), and/or dacarbazine (D) therapy. Preferably the anti-CD30 antibody drug conjugate and AVD therapy are administered every two weeks.

In various embodiments, the dose of anti-CD30 antibody drug conjugate is increased from 0.9 mg/kg to 1.8 mg/kg or 1.2 mg/kg after the Grade 2 or Grade 3 peripheral neuropathy improves to Grade 1 or less, wherein if the dose is increased to 1.2 mg/kg, the administration optionally is in combination with a chemotherapy consisting essentially of doxorubicin, vinblastine, and/or dacarbazine therapy. Preferably the anti-CD30 antibody drug conjugate and AVD therapy are administered every two weeks.

In various embodiments, the neuropathy is measured periodically using standard assays known in the art.

In various embodiments, doses of anti-CD30 antibody drug conjugate may be reduced if the patient experiences renal or hepatic impairment. In various embodiments, if the subject experiences mild hepatic impairment (Child-Pugh A) the dose is reduced to approximately 0.9 mg/kg and is administered every 2 weeks, up to a maximum of 90 mg (depending on weight of patient) administered every 2 weeks. In various embodiments, if the subject experiences mild (CrCL greater than 50-80 mL/min) or moderate (CrCL 30-50 mL/min) renal impairment, the dose of anti-CD30 antibody drug conjugate is maintained at 1.2 mg/kg up to a maximum of 120 mg every two weeks.

In various embodiments, if the anti-CD30 antibody drug conjugate is administered at 1.2 mg/kg with AVD combination therapy, the combination therapy is administered every two weeks. In various embodiments, the combination therapy is administered on days 1 and 15 of a 28 day cycle. In various embodiments, the anti-CD30 antibody drug conjugate +AVD combination therapy is administered for no more than six cycles. In various embodiments, the anti-Cd30 antibody drug conjugate +AVD combination therapy is administered for four to six cycles. In various embodiments, the anti-CD30 antibody drug conjugate +AVD therapy is administered for 4, 5, or 6 cycles.

In various embodiments, the therapy is administered until a PET scan determines there is no tumor or progression of tumor.

In various embodiments, the neuropathy is peripheral motor neuropathy or peripheral sensory neuropathy. In various embodiments, the treatment reduces one or more symptoms of peripheral neuropathy selected from the group consisting of paresthesia, hypoesthesia, polyneuropathy, muscular weakness, and demyelinating polyneuropathy.

In various embodiments, the dose of anti-CD30 antibody drug conjugate is delayed by one week or two weeks if peripheral neuropathy appears, and therapy is continued when the neuropathy is resolved or determined to be Grade 2 or less, or Grade 1 or less.

In a second aspect, the disclosure provides a method for treating a hematologic cancer in a subject comprising co-administering an anti-CD30 antibody drug conjugate with a granulopoiesis stimulating factor beginning with cycle 1 of the administration of the anti-CD30 antibody drug conjugate, or first administration of the anti-CD30 antibody drug conjugate therapy, e.g. as primary prophylaxis. In various embodiments, the granulopoiesis stimulating factor can be used also in combination with any standard or modified chemotherapeutic regimen, e.g., as a frontline therapy. For example, treatment beginning with cycle 1 of the administration of the anti-CD30 antibody drug conjugate, e.g., as primary prophylaxis, includes wherein the granulopoiesis stimulating factor is administered from within 1 day to within 7 days after beginning with cycle 1 of the administration of the anti-CD30 antibody drug conjugate. In various embodiments, the granulopoiesis stimulating factor is administered from within 1 day or 2 days to within 5 days after beginning with cycle 1 of the administration of anti-CD30 antibody drug conjugate. In some embodiments, the granulopoiesis stimulating factor is administered on the same day as the antibody drug conjugate treatment. In various embodiments, the granulopoiesis stimulating factor is administered about 24 hours to about 36 hours after each administration of, or dose of, anti-CD30 antibody drug conjugate. In various embodiments, the granulopoiesis stimulating factor is administered 24 hours to 36 hours after each administration of, or dose of, anti-CD30 antibody drug conjugate.

In various embodiments of this second aspect, the method is for reducing the incidence of neutropenia or febrile neutropenia in a subject receiving anti-CD30 antibody drug conjugate. In various embodiments, the granulopoiesis stimulating factor is administered to a subject that has not received anti-CD30 antibody drug conjugate therapy previously, or to a subject before the subject has experienced treatment-emergent neutropenia. In various embodiments, the subject has not experienced treatment-emergent grade 3-4 neutropenia after anti-CD30 antibody drug conjugate administration. In various embodiments, the subject has febrile neutropenia and is 60 years old or older.

In various embodiments of this second aspect, the method is for decreasing the incidence of infection, or for decreasing the incidence of other adverse events, in a subject receiving anti-CD30 antibody drug conjugate. In various embodiments, the granulopoiesis stimulating factor is administered to a subject that has not received anti-CD30 antibody drug conjugate therapy previously, or to a subject before the subject has experienced treatment-emergent neutropenia. In various embodiments, the subject has not experienced treatment-emergent grade 3-4 neutropenia after anti-CD30 antibody drug conjugate administration.

In various embodiments, the granulopoiesis stimulating factor is administered from 1 day to 7 days, or from 1 day to 5 days, or from 2 days to 5 days, after a second or subsequent administration of anti-CD30 antibody drug conjugate. In some embodiments, the granulopoiesis stimulating factor is administered on the same day as the second or subsequent antibody drug conjugate treatment. In various embodiments, the granulopoiesis stimulating factor is administered about 24 hours to about 36 hours after each administration of, or after each dose of, anti-CD30 antibody drug conjugate. In various embodiments, the granulopoiesis stimulating factor is administered 24 hours to 36 hours after each administration of, i.e., after each dose of, anti-CD30 antibody drug conjugate.

In various embodiments, the granulopoiesis stimulating factor is administered to a subject that has not received anti-CD30 antibody drug conjugate therapy previously, or to a subject before the subject has experienced treatment-emergent neutropenia. In various embodiments, the subject has not experienced treatment-emergent grade 3-4 neutropenia after anti-CD30 antibody drug conjugate administration.

In various embodiments, the granulopoiesis stimulating factor is granulocyte colony stimulating factor (GCSF). In various embodiments, the GCSF is a long-acting GCSF or is not long-acting GCSF. In various embodiments, the granulopoiesis stimulating factor is granulocyte monocyte colony stimulating factor (GM-CSF). In various embodiments, the GCSF is long-acting, and is administered in a single dose 1, 2 or 3 days after anti-CD30 antibody drug conjugate administration. In various embodiments, the G-CSF is administered about 24 hours to about 36 hours after each administration of anti-CD30 antibody drug conjugate. In various embodiments, the G-CSF is administered 24 hours to 36 hours after each administration of anti-CD30 antibody drug conjugate. In various embodiments, the stimulating factor is GMCSF, or the GCSF is not long acting, and is administered in multiple doses (e.g. multiple daily doses) starting at 1, 2, 3, 4, 5, 6, or 7 days after anti-CD30 antibody drug conjugate administration for a duration of at least 3, 4, 5, 6, 7, 8, 9, 10, 11, 12 or more days. In various embodiments, the granulopoiesis stimulating factor is pegfilgrastim or filgrastim.

In various embodiments, the anti-CD30 antibody drug conjugate is administered every 3 weeks.

In various embodiments, the anti-CD30 antibody drug conjugate is administered every 2 weeks. In various embodiments, anti-CD30 antibody drug conjugate is administered on day 1 and day 15 of a 28-day cycle. In various embodiments, the anti-CD30 antibody drug conjugate is administered for no more than six cycles. In various embodiments, the anti-CD30 antibody drug conjugate is administered for four to six cycles. In various embodiments, the method further comprises administering a chemotherapy consisting essentially of doxorubicin, vinblastine, and/or dacarbazine as a combination therapy, preferably A+AVD therapy, on the same day as the anti-CD30 antibody drug conjugate therapy.

In various embodiments, the anti-CD30 antibody of the anti-CD30 antibody drug conjugate comprises i) a heavy chain CDR1 set out in SEQ ID NO: 4, a heavy chain CDR2 set out in SEQ ID NO: 6, a heavy chain CDR3 set out in SEQ ID NO: 8; and ii) a light chain CDR1 set out in SEQ ID NO: 12, a light chain CDR2 set out in SEQ ID NO: 14, and a light chain CDR13 set out in SEQ ID NO: 16.

In various embodiments, the anti-CD30 antibody of the anti-CD30 antibody drug conjugate also comprises i) an amino acid sequence at least 85% identical to a heavy chain variable region set out in SEQ ID NO: 2 and ii) an amino acid sequence at least 85% identical to a light chain variable region set out in SEQ ID NO: 10. It is contemplated that the amino acid variable region sequence can be 90%, 95%, 96% 97%, 98% or 99% identical to either SEQ ID NO: 2 or SEQ ID NO: 10.

In various embodiments, the anti-CD30 antibody of the anti-CD30 antibody drug conjugate is a monoclonal anti-CD30 antibody. In various embodiments, the anti-CD30 antibody of the anti-CD30 antibody drug conjugate is a chimeric AC10 antibody.

In various embodiments, the antibody drug conjugate comprises monomethyl auristatin E and a protease-cleavable linker. In various embodiments, the protease cleavable linker is comprises a thiolreactive spacer and a dipeptide. In various embodiments, the protease cleavable linker consists of a thiolreactive maleimidocaproyl spacer, a valine-citrulline dipeptide, and a p-amino-benzyloxycarbonyl spacer.

In various embodiments, the antibody is an IgG antibody, preferably an IgG1 antibody.

In various embodiments, the anti-CD30 antibody drug conjugate is brentuximab vedotin.

In various embodiments, the subject is also receiving a chemotherapy consisting essentially of doxorubicin, vinblastine, and dacarbazine (AVD) as a combination therapy.

In various embodiments, the anti-CD30 antibody drug conjugate is brentuximab vedotin and is administered at 1.2 mg/kg, doxorubicin is administered at 25 mg/m$^2$, vinblastine is administered at 6 mg/m$^2$, and dacarbazine is administered at 375 mg/m$^2$.

In various embodiments, the granulopoiesis stimulating factor, e.g., G-CSF is administered in a dose range from 5 to 10 mcg/kg/day, or 300 to 600 mcg/day. In various embodiments, the granulopoiesis stimulating factor is administered at a dose of 6 mg/dose. In various embodiments, the G-CSF is administered about 24 hours to about 36 hours after each administration of anti-CD30 antibody drug conjugate, wherein the subject is also receiving AVD therapy.

In various embodiments, the granulopoiesis stimulating factor is given intravenously or subcutaneously. In various embodiments, the granulopoiesis stimulating factor is given in a single dose or multiple doses, for example, a long-acting GCSF may be administered in a single dose or multiple doses on the same day, and a non-long-acting GCSF may be given in multiple doses over multiple days.

In any of the aspects disclosed herein, the subject has a hematologic cancer. In various embodiments, the hematologic cancer is selected from the group consisting of classical Hodgkin Lymphoma, non-Hodgkin Lymphoma, cutaneous T-cell lymphoma (CTCL), and anaplastic large cell lymphoma (ALCL).

In various embodiments, the hematologic cancer is classical Hodgkin Lymphoma. In various embodiments, the hematologic cancer is a stage III or IV classical Hodgkin Lymphoma. In various embodiments, the hematologic cancer of the subject has not been treated.

In various embodiments, the anaplastic large cell lymphoma (ALCL) is a systemic anaplastic large cell lymphoma (sALCL).

In various embodiments, the cutaneous T-cell lymphoma (CTCL) is a mycosis fungoides (MF). In various embodiments, the mycosis fungoides (MF) is a CD30-positive mycosis fungoides (MF).

In various embodiments, the cutaneous T-cell lymphoma (CTCL) is a primary cutaneous anaplastic large cell lymphoma (pcALCL).

In various embodiments, the subject has received prior systemic therapy.

In a third aspect, the disclosure provides a method of treating a subject having advanced classical Hodgkin Lymphoma comprising administering as frontline treatment an effective amount of a composition comprising bretuximab vedotin in combination with AVD therapy consisting of doxorubicin, vinblastine, and dacarbazine, wherein the brentuximab vedotin is administered at 1.2 mg/kg every two weeks, doxorubicin is administered at 25 mg/m$^2$ every two weeks, vinblastine is administered at 6 mg/m$^2$ every two weeks, and dacarbazine is administered at 375 mg/m$^2$ every two weeks, preferably on days 1 and 15 of a 28 day cycle, until a maximum of six cycles, and wherein the brentuximab vedotin is administered within about 1 hour after administration of the AVD therapy; optionally the subject is characterized by one or more of the following: (1) Stage 4 Hodgkin Lymphoma, (2) t has HL involving at least 1 extranodal site, e.g., at least 1, 2 or 3 extranodal sites, (3) less than 60 years old or less than 65 years old, (4) an International Prognostic Score of 4 to 7 [4, 5, 6, 7], or (5) an Eastern Cooperative Oncology Group (ECOG) performance status prior to therapy of 2 or less. The methods herein further provide that progression free survival (PFS) of the subject after therapy is maintained for greater than 1 year. In various embodiments, the progression free survival (PFS) of the subject after therapy is maintained for approximately 2 years. In certain embodiments, after four to six cycles of A+AVD therapy the subject has a Deauville score of 3 or less, or 2 or less.

In another aspect, the disclosure provides an anti-CD30 antibody drug conjugate for use in treating a subject that has exhibited Grade 2 or greater peripheral neuropathy after starting anti-CD30 antibody drug conjugate therapy at a dose of 1.2 mg/kg or more, wherein said patients is administered anti-CD30 antibody drug conjugate at a dose of 0.9 mg/kg.

In a further aspect, contemplated herein is an anti-CD30 antibody drug conjugate for use in treating a hematologic cancer in a subject comprising administering an anti-CD30 antibody drug conjugate and prophylactically administering a granulopoiesis stimulating factor, wherein the stimulating factor is administered from 1 day to 7 days after beginning with cycle 1 of the administration of the anti-CD30 antibody drug conjugate.

In a related aspect, also contemplated is an anti-CD30 antibody drug conjugate for use in reducing the incidence of neutropenia, infection or other adverse events in a subject receiving treatment with an anti-CD30 antibody drug conjugate comprising prophylactically administering to the subject a granulopoiesis stimulating factor, wherein the stimulating factor is administered from 1 day to 7 days after beginning with cycle 1 of the administration of the anti-CD30 antibody drug conjugate. In various embodiments, the granulopoiesis stimulating factor is administered about 24 hours to about 36 hours after each administration of anti-CD30 antibody drug conjugate, optionally anti-CD30 antibody drug conjugate in combination with a chemotherapy regimen described herein. In various embodiments, the granulopoiesis stimulating factor is a long acting G-CSF. In various embodiments, the G-CSF is administered 24 hours to 36 hours after each administration of anti-CD30 antibody drug conjugate.

It is specifically provided herein that all aspects of the disclosure described above with the methods of treatment are applicable to the anti-CD30 antibody drug conjugate for use in any of the indications described above.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE FIGURES

FIG. 1. Modified Progression-free Survival in the Intent-to-treat Population. FIG. 1A shows Kaplan-Meier estimates of modified progression-free survival, by treatment group, according to the independent review facility.

FIG. 2 (Table 1). Baseline Patient Demographics and Clinical Characteristics (Intent-to-treat Population).

FIG. 3 (Table 2). Summary of Subsequent Therapy and End-of-treatment Deauville Scores for Events Noted in Modified Progression-free Survival per Independent Review Facility and Correlation with Events Noted by Trial Investigators (Intent-to-treat Population).

FIG. 4 (Table 3). Summary of Response in the Intent-to-treat Population.

FIG. 5 (Table 4). Summary of Adverse Events in the Safety Population.

FIG. 7. Details of Brentuximab Vedotin Dose Modifications.

FIG. 8. Summary of First Subsequent Chemotherapy for Patients Failing to Achieve a Complete Response at the Completion of Frontline Therapy.

FIG. 9. Summary of Reasons for Switching to Alternative Chemotherapy during Frontline Therapy (Safety Population).

FIG. 10. Exposure to, and Dose Modifications of, Individual Regimen Components.

FIG. 11. Summary of Peripheral Neuropathy (SMQ) (Safety Population).

DETAILED DESCRIPTION

Figure 1B:
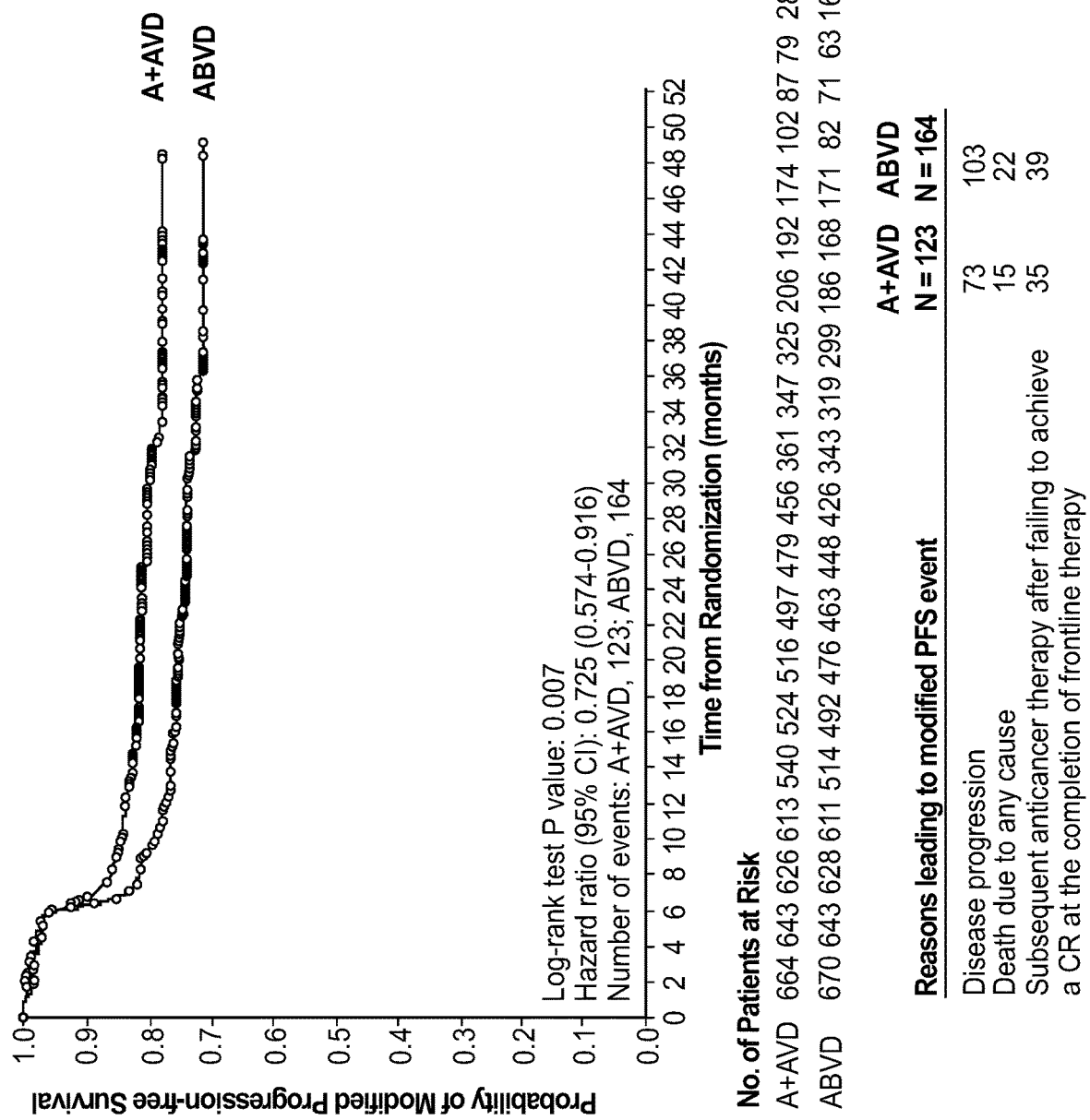
FIG. 1B shows Kaplan-Meier estimates of modified progression-free survival, by treatment group according to investigators.
Figure 1C:
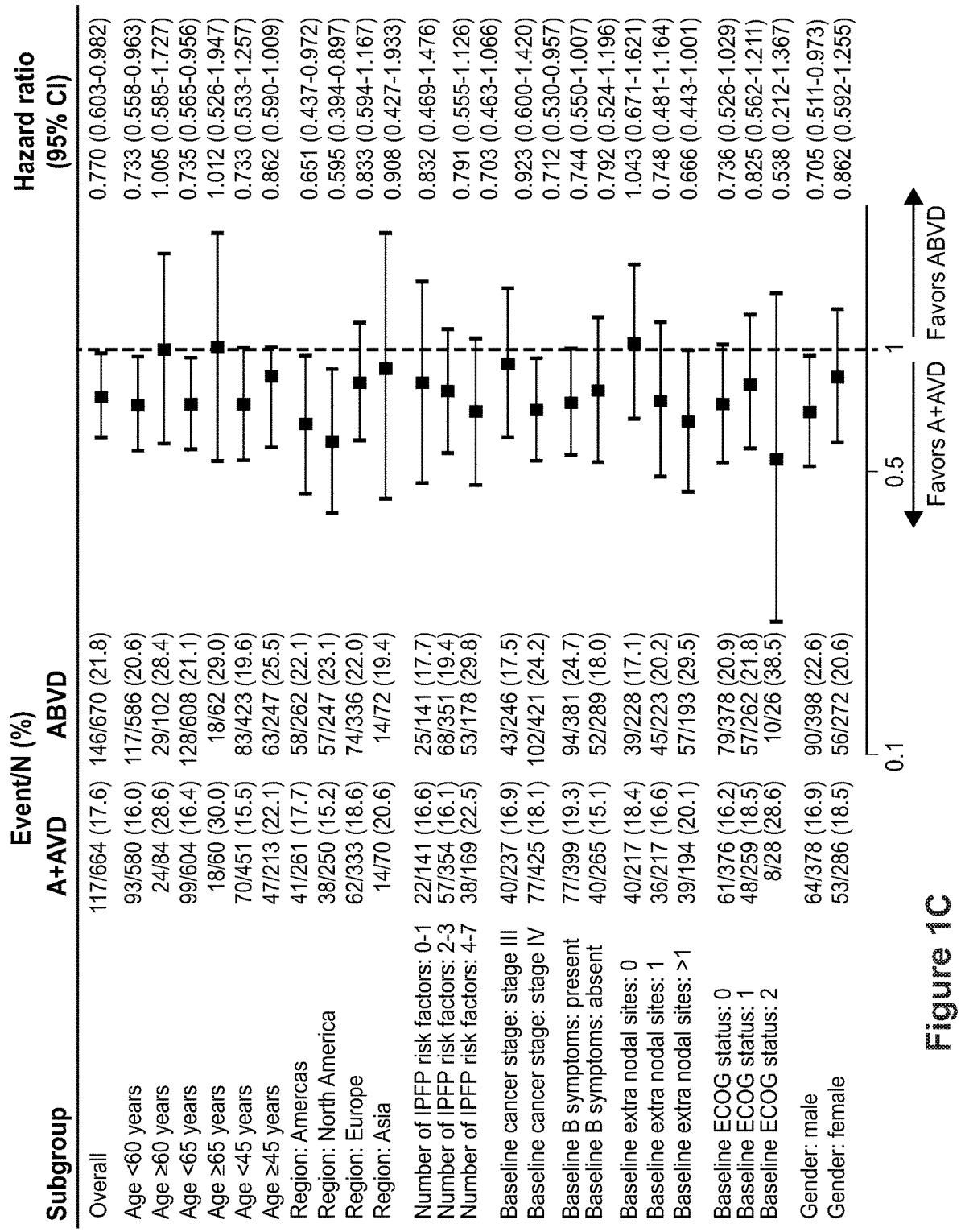
FIG. 1C shows the forest plot analysis of modified progression-free survival according to the independent review facility in key pre-specified subgroups. The intent-to-treat population included all patients who underwent randomization.

The present disclosure provides methods for improving adverse events associated with treatment of cancers with an anti-CD30 antibody drug conjugate. The regimens described herein are effective for reducing peripheral neuropathy in treated patients as well as improving incidence of neutropenia, and/or febrile neutropenia, and/or infection associated with therapy.

Definitions

Unless otherwise defined, all technical and scientific terms used herein have the same meaning as commonly understood by one of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

As used herein and in the appended claims, the singular forms "a," "and," and "the" include plural referents unless the context clearly dictates otherwise. Thus, for example, reference to "a derivative" includes a plurality of such derivatives and reference to "a subject" includes reference to one or more subjects and so forth.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

"Therapeutically effective amount" as used herein refers to that amount of an agent effective to produce the intended beneficial effect on health.

"Antibody +AVD therapy", or "A+AVD therapy" as used herein refers to treatment of a subject with an anti-CD30 antibody drug conjugate as described herein in combination with chemotherapy consisting essentially of doxorubicin, vinblastine, and dacarbazine (AVD therapy).

"Lymphoma" as used herein is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sezary's disease, peripheral T-cell lymphomas not otherwise specified, nodular sclerosis of Hodgkin lymphoma, and mixed-cellularity subtype of Hodgkin lymphoma.

"Leukemia" as the term is used herein is a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocyctic leukemia (AMoL). Other leukemias include hairy cell leukemia (HCL), T-cell lymphatic leukemia (T-PLL), large granular lymphocytic leukemia and adult T-cell leukemia.

"Prophylactic" or "primary prophylaxis" as used herein refers to administration of an agent, such as a colony stimulating factor or granulopoiesis stimulating factor, prior to onset of neutropenia or symptoms of neutropenia in a subject. It is contemplated that prophylaxis includes administration of the granulopoeisis stimulating factor at the beginning of cycle 1 of administration of anti-CD30 conjugate therapy, or first administration of the anti-CD30-antibody drug conjugate therapy, optionally in combination with a chemotherapy consisting essentially of doxorubicin, vinblastine, and/or dacarbazine (AVD therapy). The term "beginning with cycle 1 of the administration of the anti-CD30 antibody drug conjugate" and "first administration of the anti-CD30 antibody drug conjugate" are used interchangeably herein in reference to treatment with granulopoiesis stimulating factor.

"Granulopoiesis stimulating factor" as used herein refers to an agent such as a cytokine or other growth factor that can induce production of neutrophils and other granulocytes. Exemplary granulopoiesis stimulating factors include, but are not limited to, granulocyte-colony stimulating factor (GCSF) and derivatives thereof, such as filgrastim and the long-acting GCSF PEG-filgrastim, or granulocyte-monocyte colony stimulating factor (GMCSF).

"Neutropenia" as used herein refers to an abnormally low concentration of neutrophils in the blood. "Reducing the incidence of neutropenia in a subject" refers to decreasing the number of neutropenia incidents in a subject receiving treatment and/or reducing the severity of neutropenic incidents in a subject. "Preventing neutropenia" refers to preventing or inhibiting the onset of neutropenia, e.g., as a result of prophylactic treatment with a granulopoiesis stimulating factor. Normal reference range for absolute neutrophil count (ANC) in adults is 1500 to 8000 cells per microliter (µl) of blood. Neutropenia can be categorized as follows: mild neutropenia (1000⇐ANC<1500); moderate neutropenia (500⇐ANC<1000); severe neutropenia (ANC<500). Hsieh et al., Ann. Intern. Med. 146:486-92, 2007.

The term "pharmaceutically acceptable" as used herein refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term "pharmaceutically compatible ingredient" refers to a pharmaceutically acceptable diluent, adjuvant, excipient, or vehicle with which an antibody-drug conjugate is administered.

The terms "specific binding" and "specifically binds" mean that the anti-CD30 antibody will react, in a highly selective manner, with its corresponding target, CD30, and not with the multitude of other antigens.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In certain embodiments, the two sequences are the same length.

The term "substantially identical," in the context of two nucleic acids or polypeptides, refers to two or more sequences or subsequences that have at least 70% or at least 75% identity; more typically at least 80% or at least 85% identity; and even more typically at least 90%, at least 95%, or at least 98% identity (for example, as determined using one of the methods set forth below).

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. 85:2444-8. Alternatively, protein sequence alignment may be carried out using the CLUSTAL W algorithm, as described by Higgins et al., 1996, Methods Enzymol. 266: 383-402.

The abbreviation "MMAE" refers to monomethyl auristatin E.

The abbreviations "vc" and "val-cit" refer to the dipeptide valine-citrulline.

The abbreviation "PAB" refers to the self-immolative spacer:

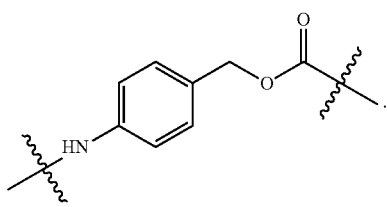 [SMILES: *Nc1ccc(COC(*)=O)cc1]

The abbreviation "MC" refers to the stretcher maleimidocaproyl:

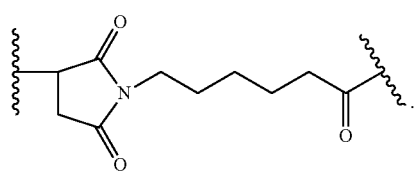 [SMILES: *C(=O)CCCCCN1C(=O)CC(*)C1=O]

cA010-MC-vc-PAB-MMAE refers to a chimeric AC10 antibody conjugated to the drug MMAE through a MC-vc-PAB linker.

An anti-CD30 MC-vc-PAB-MMAE antibody-drug conjugate refers to an anti-CD30 antibody conjugated to the drug MMAE via a linker comprising the dipeptide valine citrulline and the self-immolative spacer PAB as shown in Formula (I) of U.S. Pat. No. 9,211,319.

Antibodies

Murine anti-CD30 mAbs known in the art have been generated by immunization of mice with Hodgkin's disease (HD) cell lines or purified CD30 antigen. AC10, originally termed 010 (Bowen et al., 1993, J. Immunol. 151:5896 5906), is distinct in that this anti-CD30 mAb that was prepared against a hum an NK-like cell line, YT (Bowen et al., 1993, J. Immunol. 151:5896 5906). Initially, the signaling activity of this mAb was evidenced by the down regulation of the cell surface expression of CD28 and CD45 molecules, the up regulation of cell surface CD25 expression and the induction of homotypic adhesion following binding of 010 to YT cells. Sequences of the AC10 antibody are set out in SEQ ID NO: 1-16 and Table A below. See also U.S. Pat. No. 7,090,843, incorporated herein by reference, which discloses a chimeric AC10 antibody.

Generally, antibodies of the disclosure immunospecifically bind CD30 and exert cytostatic and cytotoxic effects on malignant cells in Hodgkin's disease. Antibodies of the disclosure are preferably monoclonal, and may be multispecific, human, humanized or chimeric antibodies, single chain antibodies, Fab fragments, F(ab') fragments, fragments produced by a Fab expression library, and CD30 binding fragments of any of the above. The term "antibody," as used herein, refers to immunoglobulin molecules and immunologically active portions of immunoglobulin molecules, i.e., molecules that contain an antigen binding site that immunospecifically binds CD30. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the antibodies are human antigen-binding antibody fragments of the present disclosure and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, CH1, CH2, CH3 and CL domains. Also included in the disclosure are antigen-binding fragments also comprising any combination of variable region(s) with a hinge region, CH1, CH2, CH3 and CL domains. Preferably, the antibodies are human, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. No. 5,939,598 by Kucherlapati et al.

The antibodies of the present disclosure may be monospecific, bispecific, trispecific or of greater multi specificity. Multispecific antibodies may be specific for different epitopes of CD30 or may be specific for both CD30 as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Antibodies of the present disclosure may be described or specified in terms of the particular CDRs they comprise. In certain embodiments antibodies of the disclosure comprise one or more CDRs of AC10. The disclosure encompasses an antibody or derivative thereof comprising a heavy or light chain variable domain, said variable domain comprising (a) a set of three CDRs, in which said set of CDRs are from monoclonal antibody AC10, and (b) a set of four framework regions, in which said set of framework regions differs from the set of framework regions in monoclonal antibody AC 10, and in which said antibody or derivative thereof immunospecifically binds CD30.

In a specific embodiment, the disclosure encompasses an antibody or derivative thereof comprising a heavy chain variable domain, said variable domain comprising (a) a set of three CDRs, in which said set of CDRs comprises SEQ ID NO:4, 6, or 8 and (b) a set of four framework regions, in which said set of framework regions differs from the set of framework regions in monoclonal antibody AC10, and in which said antibody or derivative thereof immunospecifically binds CD30.

In various embodiments, the invention encompasses an antibody or derivative thereof comprising a light chain variable domain, said variable domain comprising (a) a set of three CDRs, in which said set of CDRs comprises SEQ ID NO:12, 14 or 16, and (b) a set of four framework regions, in which said set of framework regions differs from the set of framework regions in monoclonal antibody AC10, and in which said antibody or derivative thereof immunospecifically binds CD30.

Additionally, antibodies of the present disclosure may also be described or specified in terms of their primary structures. Antibodies having at least 50%, at least 55%, at least 60%, at least 65%, at least 70%, at least 75%, at least 80%, at least 85%, at least 90%, at least 95% and most preferably at least 98% identity (as calculated using methods known in the art and described herein) to the variable regions of AC10 are also included in the present invention, and preferably include the CDRs of AC10. Antibodies of the present invention may also be described or specified in terms of their binding affinity to CD30. Preferred binding affinities include those with a dissociation constant or Kd less than $5\times10^2$ M, $10^{-2}$ M, $5\times10^{-3}$ M, $10^{-3}$ M, $5\times10^{-4}$ M, $10^4$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$M, $5\times10^{-9}$M, $10^{-9}$ M, $5\times10^{-10}$M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The antibodies also include derivatives that are modified, i.e., by the covalent attachment of any type of molecule to the antibody such that covalent attachment does not prevent the antibody from binding to CD30 or from exerting a cytostatic or cytotoxic effect on Hodgkin's Disease cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The invention further provides nucleic acids comprising a nucleotide sequence encoding a protein, including but not limited to, a protein of the invention and fragments thereof. Nucleic acids of the invention preferably encode one or more CDRs of antibodies that bind to CD30 and exert cytotoxic or cytostatic effects on HD cells. Exemplary nucleic acids of the invention comprise SEQ ID NO:3, SEQ ID NO:5, SEQ ID NO:7, SEQ ID NO:11, SEQ ID NO:13, or SEQ ID NO:15. Variable region nucleic acids of the invention comprise SEQ ID NO:1 or SEQ ID NO:9. (See Table A).

TABLE A

| MOLECULE | NUCLEOTIDE OR AMINO ACID | SEQ ID NO |
|---|---|---|
| AC 10 Heavy Chain Variable Region | Nucleotide | 1 |
| AC 10 Heavy Chain Variable Region | Amino Acid | 2 |
| AC 10 Heavy Chain-CDR1 (H1) | Nucleotide | 3 |
| AC 10 Heavy Chain-CDR1 (H1) | Amino Acid | 4 |
| AC 10 Heavy Chain-CDR2 (H2) | Nucleotide | 5 |
| AC 10 Heavy Chain-CDR2 (H2) | Amino Acid | 6 |
| AC 10 Heavy Chain-CDR3 (H3) | Nucleotide | 7 |
| AC 10 Heavy Chain-CDR3 (H3) | Amino Acid | 8 |
| AC 10 Light Chain Variable Region | Nucleotide | 9 |
| AC 10 Light Chain Variable Region | Amino Acid | 10 |
| AC 10 Light Chain-CDR1 (L1) | Nucleotide | 11 |
| AC 10 Light Chain-CDR1 (L1) | Amino Acid | 12 |
| AC 10 Light Chain-CDR2 (L2) | Nucleotide | 13 |
| AC 10 Light Chain-CDR2 (L2) | Amino Acid | 14 |
| AC 10 Light Chain-CDR3 (L3) | Nucleotide | 15 |
| AC 10 Light Chain-CDR3 (L3) | Amino Acid | 16 |

In various embodiments, the antibody is an IgG antibody, e.g. an IgG1, IgG2, IgG3 or IgG4 antibody, preferably an IgG1 antibody.

Antibody-Drug Conjugates

Contemplated herein is the use of antibody drug conjugates comprising an anti-CD30 antibody, covalently linked to MMAE through a MC-vc-PAB linker. The antibody drug conjugates are delivered to the subject as a pharmaceutical composition. The anti-CD30 antibody drug conjugates are described in U.S. Pat. No. 9,211,319, herein incorporated by reference.

In various embodiments, the anti-CD30 antibody-drug conjugates of the present invention have the following formula:

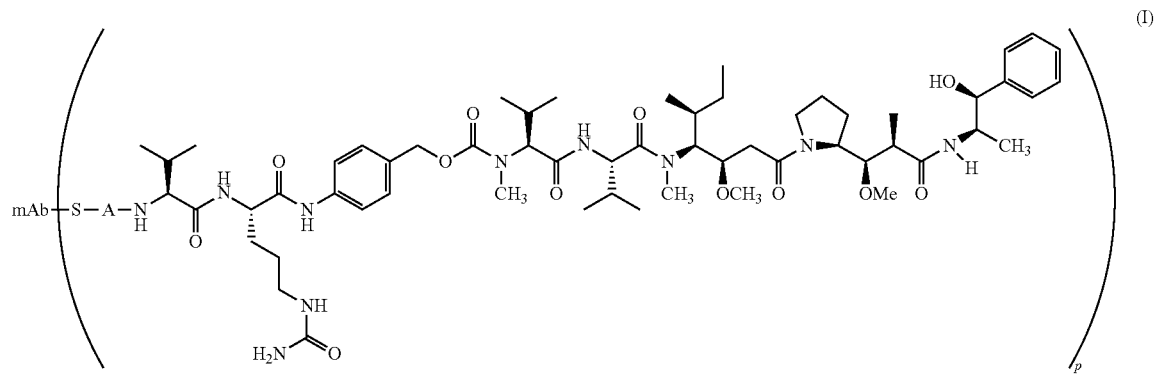

or a pharmaceutically acceptable salt thereof; wherein: mAb is an anti-CD30 antibody, S is a sulfur atom of the antibody A- is a Stretcher unit, p is from about 3 to about 5.

The drug loading is represented by p, the average number of drug molecules per antibody in a pharmaceutical composition. For example, if p is about 4, the average drug loading taking into account all of the antibody present in the pharmaceutical composition is about 4. P ranges from about 3 to about 5, more preferably from about 3.6 to about 4.4, even more preferably from about 3.8 to about 4.2. P can be about 3, about 4, or about 5. The average number of drugs per antibody in preparation of conjugation reactions may be characterized by conventional means such as mass spectroscopy, ELISA assay, and HPLC. The quantitative distribution of antibody-drug conjugates in terms of p may also be determined. In some instances, separation, purification, and characterization of homogeneous antibody-drug-conjugates where p is a certain value from antibody-drug-conjugates with other drug loadings may be achieved by means such as reverse phase HPLC or electrophoresis.

The Stretcher unit (A), is capable of linking an antibody unit to the valine-citrulline amino acid unit via a sulfhydryl group of the antibody. Sulfhydryl groups can be generated, for example, by reduction of the interchain disulfide bonds of an anti-CD30 antibody. For example, the Stretcher unit can be linked to the antibody via the sulfur atoms generated from reduction of the interchain disulfide bonds of the antibody. In some embodiments, the Stretcher units are linked to the antibody solely via the sulfur atoms generated from reduction of the interchain disulfide bonds of the antibody. In some embodiments, sulfhydryl groups can be generated by reaction of an amino group of a lysine moiety of an anti-CD30 antibody with 2-iminothiolane (Traut's reagent) or other sulfhydryl generating reagents. In certain embodiments, the anti-CD30 antibody is a recombinant antibody and is engineered to carry one or more lysines. In certain other embodiments, the recombinant anti-CD30 antibody is engineered to carry additional sulfhydryl groups, e.g., additional cysteines.

The synthesis and structure of MMAE is described in U.S. Pat. No. 6,884,869 incorporated by reference herein in its entirety and for all purposes. The synthesis and structure of exemplary Stretcher units and methods for making antibody drug conjugates are described in, for example, U.S. Publication Nos. 2006/0074008 and 2009/0010945 each of which is incorporated herein by reference in its entirety.

Representative Stretcher units are described within the square brackets of Formulas IIIa and IIIb of U.S. Pat. No. 9,211,319, and incorporated herein by reference.

In various embodiments, the anti-CD30 antibody drug conjugate comprises monomethyl auristatin E and a protease-cleavable linker. It is contemplated that the protease cleavable linker is comprises a thiolreactive spacer and a dipeptide. In various embodiments, the protease cleavable linker consists of a thiolreactive maleimidocaproyl spacer, a valine-citrulline dipeptide, and a p-amino-benzyloxycarbonyl spacer.

In a preferred embodiment, the anti-CD30 antibody drug conjugate is brentuximab vedotin, having the structure:

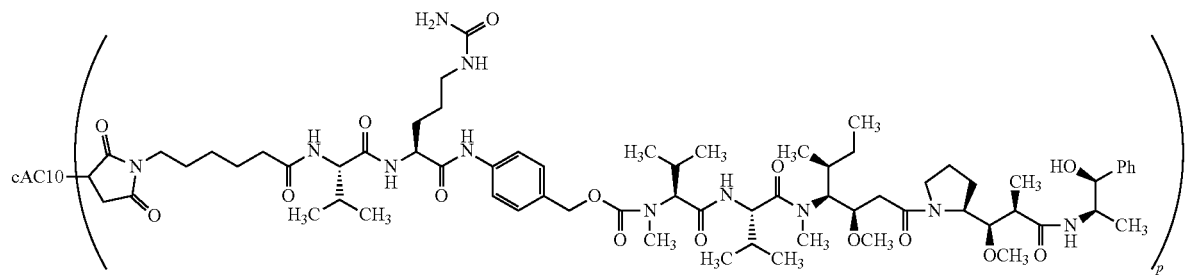

Brentuximab vedotin is a CD30-directed antibody-drug conjugate consisting of three components: (i) the chimeric IgG1 antibody cAC10, specific for human CD30, (ii) the microtubule disrupting agent MMAE, and (iii) a protease-cleavable linker that covalently attaches MMAE to cAC10. The drug to antibody ratio or drug loading is represented by "p" in the structure of brentuximab vedotin and ranges in integer values from 1 to 8. The average drug loading brentuximab vedotin in a pharmaceutical composition is about 4.

Methods of Use

Provided herein are improved methods for administering anti-CD30 antibody-drug conjugate. Disclosed herein are methods for reducing adverse events in a subject having a hematologic cancer during administration of an anti-CD30 antibody drug conjugate, optionally in combination with a chemotherapy regimen. In various embodiments, the chemotherapy regimen consists essentially of doxorubicin, vinblastine, and/or dacarbazine, preferably as A+AVD therapy.

Additional chemotherapeutic agents are disclosed in the following table and may be used alone or in combination with one or more additional chemotherapeutic agents, which in turn can also be administered in combination with an anti-CD30 antibody drug conjugate.

| Chemotherapeutic Agents | |
|---|---|
| Alkylating agents | Natural products |
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| Nitrosoureas | vindesine |
| carmustine (BCNU) | vinorelbin |
| lomustine (CCNU) | Taxotere ® (docetaxel) |
| semustine (methyl-CCNU) | estramustine |
| Ethylenimine/Methyl-melamine | estramustine phosphate |
| thriethylenemelamine (TEM) | Epipodophylotoxins |
| triethylene thiophosphoramide (thiotepa) | etoposide |
| | teniposide |
| hexamethylmelamine (HMM, altretamine) | Antibiotics |
| | actimomycin D |
| Alkyl sulfonates | daunomycin (rubido-mycin) |
| busulfan | doxorubicin (adria-mycin) |
| Triazines | mitoxantrone |
| dacarbazine (DTIC) | idarubicin |
| Antimetabolites | epirubicin |
| Folic Acid analogs | valrubicin |
| methotrexate | bleomycin |
| Trimetrexate | splicamycin (mithramycin) |
| Pemetrexed (Multi-targeted antifolate) | mitomycinC |
| | dactinomycin |
| Pyrimidine analogs | aphidicolin |
| 5-fluorouracil | Enzymes |
| fluorodeoxyuridine | L-asparaginase |
| gemcitabine | L-arginase |
| cytosine arabinoside (AraC, cytarabine) | Radiosensitizers |
| | metronidazole |
| 5-azacytidine | misonidazole |
| 2,2'-difluorodeoxy-cytidine | desmethylmisonidazole |
| Purine analogs | pimonidazole |
| 6-mercaptopurine | etanidazole |
| 6-thioguanine | nimorazole |
| azathioprine | RSU 1069 |
| 2'-deoxycoformycin (pentostatin) | EO9 |
| | RB 6145 |
| erythrohydroxynonyl-adenine (EHNA) | SR4233 |
| fludarabine phosphate | nicotinamide |
| 2-chlorodeoxyadenosine (cladribine, 2-CdA) | 5-bromodeozyuridine |
| | 5-iododeoxyuridine |
| Type I Topoisomerase Inhibitors | bromodeoxycytidine |
| camptothecin | Miscellaneous agents |
| topotecan | bisphosphonates |
| irinotecan | RANKL inhibitor |
| Biological response modifiers | denosumab |
| G-CSF | Platinium coordination complexes |
| GM-CSF | cisplatin |
| Differentiation Agents | carboplatin |
| retinoic acid derivatives | oxaliplatin |
| Hormones and antagonists | nthracenedione |
| Adrenocorticosteroids/antagonists | mitoxantrone |
| calcitonin | Substituted urea |
| prednisone and equiv-alents | hydroxyurea |
| dexamethasone | Methylhydrazine derivatives |
| ainoglutethimide | N-methylhydrazine (MIH) |

| Chemotherapeutic Agents | |
|---|---|
| Progestins | procarbazine |
| hydroxyprogesterone caproate | Adrenocortical suppressant |
| medroxyprogesterone acetate | mitotane (o,p'-DDD) |
| megestrol acetate | ainoglutethimide |
| Estrogens | Cytokines |
| diethylstilbestrol | interferon (α, β, γ) |
| ethynyl estradiol/equivalents | interleukin-2 |
| Antiestrogen | Photosensitizers |
| tamoxifen | hematoporphyrin derivatives |
| Androgens | Photofrin ® |
| testosterone propionate | benzoporphyrin derivatives |
| fluoxymesterone/equivalents | Npe6 |
| Antiandrogens | tin etioporphyrin (SnET2) |
| flutamide | pheoboride-a |
| gonadotropin-releasing hormone analogs | bacteriochlorophyll-a |
| | naphthalocyanines |
| leuprolide | phthalocyanines |
| Nonsteroidal antiandrogens | zinc phthalocyanines |
| flutamide | Radiation |
| Histone Deacetylase Inhibitors | X-ray |
| Vorinostat | ultraviolet light |
| Romidepsin | gamma radiation |
| | visible light |
| | infrared radiation |
| | microwave radiation |

A hematological cancer refers to a cancer that starts in blood forming tissue, or in cells of the immune system. A CD30-expressing hematologic cancer refers to a hematologic cancer that expresses the CD30 antigen. The CD30 antigen is expressed in large numbers on tumor cells of select lymphomas and leukemias. Hematological cancers such as classical Hodgkin lymphoma, non-Hodgkin lymphoma, anaplastic large-cell lymphoma, and cutaneous T-cell lymphoma (CTCL), are examples of hematologic cancers that can be treated by the present methods.

In any of the aspects or embodiments herein, the methods herein provide for treating a subject who is newly diagnosed and has not previously been treated for a hematologic cancer, or a subject who has relapsed. It is contemplated that the subject has advanced classic Hodgkin Lymphoma (e.g., Stage III or Stage IV).

In various embodiments, the disclosure provides a method of treating a subject having advanced (Grade 3/4), newly diagnosed classical Hodgkin Lymphoma (HL) comprising administering an effective amount of a composition comprising brentuximab vedotin (A) in combination with a chemotherapy consisting essentially of doxorubicin, vinblastine, and dacarbazine (AVD therapy), wherein the brentuximab vedotin is administered at 1.2 mg/kg, doxorubicin is administered at 25 mg/m², vinblastine is administered at 6 mg/m², and dacarbazine is administered at 375 mg/m², and wherein the brentuximab vedotin is administered within 1 hour after administration of the AVD therapy. It is shown herein that the treatment above appears to have increased efficacy in subjects characterized by one or more of the following: (1) Stage 4 Hodgkin Lymphoma, (2) HL involving at least 1 extranodal site, e.g., at least 1, 2 or 3 extranodal sites, (3) an International Prognostic Score of 4 to 7 [4, 5, 6, 7], (4) an Eastern Cooperative Oncology Group (ECOG) performance status prior to therapy of 2 or less, (5) is less than 60 years old or less than 65 years old. The methods herein further provide progression free survival (PFS) of the subject after therapy is maintained for greater than 1 year. In various embodiments, the progression free survival (PFS) of the subject after therapy is maintained for approximately 2 years. In certain embodiments, after four to six cycles of A+AVD therapy the subject has a Deauville score of 3 or less, or 2 or less. In certain embodiments, after two cycles of therapy [i.e., four administrations] the subject has a Deauville score of 1 or 2.

Peripheral Neuropathy

Peripheral neuropathy develops as a result of damage to the peripheral nervous system during treatment with anti-CD30 antibody drug conjugate. Symptoms include numbness or tingling, pricking sensations (paresthesia), and muscle weakness. Motor nerve damage is most commonly associated with muscle weakness.

Provided herein is a method for treating a subject that has exhibited Grade 2 or greater peripheral neuropathy after starting administration of anti-CD30 antibody drug conjugate, e.g. brentuximab vedotin, at a dose of 1.2 mg/kg or more, comprising administering the anti-CD30 antibody drug conjugate at a dose of 0.9 mg/kg. In various embodiments, when the subject exhibits Grade 3 neuropathy, the administration of the anti-CD30 antibody drug conjugate, e.g., brentuximab vedotin, is withheld until peripheral neuropathy decreases to Grade 2 or lower and then 0.9 mg/kg of the anti-CD30 antibody drug conjugate is administered. In some embodiments, the reduced dose of 0.9 mg/kg is given up to a maximum dose of 90 mg every 2 weeks.

In various embodiments, when the subject exhibits Grade 3 neuropathy, the administration of anti-CD30 antibody drug conjugate is reduced, e.g., to 0.9 mg/kg, until peripheral neuropathy decreases to Grade 2 or less and then 0.9 mg/kg anti-CD30 antibody drug conjugate is administered or maintained.

In certain embodiments, the subject exhibited Grade 2 or 3 peripheral neuropathy after starting anti-CD30 antibody drug conjugate administration at a dose of 1.8 mg/kg. In various embodiments, the subject exhibited Grade 2 or 3 peripheral neuropathy after starting anti-CD30 antibody drug conjugate administration at a dose of 1.2 mg/kg, optionally in combination with a chemotherapy consisting essentially of doxorubicin, vinblastine, and dacarbazine (AVD) as a combination therapy.

In certain embodiments, the dose of anti-CD30 antibody drug conjugate is increased to 1.8 mg/kg or 1.2 mg/kg after the Grade 2 or Grade 3 peripheral neuropathy improves to Grade 1 or less, wherein if the dose is increased to 1.2 mg/kg, the administration optionally is in combination with a chemotherapy consisting essentially of doxorubicin, vinblastine, and dacarbazine (AVD) as a combination therapy. In certain embodiments, when the peripheral neuropathy is a Grade 2, the reduced dose of 0.9 mg/kg is given up to a maximum dose of 90 mg every 2 weeks.

Methods for measuring neuropathy are known in the art and utilized by the treating physician to monitor and diagnose neuropathy in a subject receiving anti-CD30 antibody drug conjugate therapy. For example, the National Cancer Information Center-Common Toxicity Criteria (NCIC-CCT) describes Grade 1 PN as characterized by mild paresthesias and/or loss of deep tendon flexion; Grade 2 PN is characterized by mile or moderate objective sensory loss and/or moderate paresthesias; Grade 3 PN is characterized by sensory loss and/or paresthesias that interferes with function. Grade 4 PN is characterized by paralysis.

In various embodiments, if the anti-CD30 antibody drug conjugate is administered at 1.2 mg/kg with AVD combination therapy, the combination therapy is administered every two weeks. For example, the combination therapy is administered on days 1 and 15 of a 28 day cycle.

In various embodiments, the anti-CD30 antibody drug conjugate +AVD combination therapy is administered for no more than six cycles, for examples from 4 to 6 cycles, or for 4, 5 or 6 cycles.

It is contemplated that the therapy is administered until a PET scan determines there is no tumor or progression of tumor. If after the end of treatment, e.g., 4 to 6 cycles, the PET scan still shows some tumor, the treating physician may repeat the course of treatment as necessary until the PET scan is negative or shows slowed or no tumor progression. The repeat of cycles may begin after no break, or after 1, 2, 3, 4, 5, 6 or more weeks after the initial treatment with A+AVD therapy.

In various embodiments, anti-CD30 antibody drug conjugate, e.g., brentuximab vedotin, therapy is administered by intravenous infusion over the course of 30 minutes. In certain embodiments, the anti-CD30 antibody drug conjugate is administered at 1.2 mg/kg to a maximum of 120 mg in combination with AVD therapy.

The treatment is useful to treat peripheral motor neuropathy or peripheral sensory neuropathy. The treatment reduces one or more symptoms of peripheral neuropathy, including but not limited to, paresthesia, hypoesthesia, polyneuropathy, muscular weakness, and demyelinating polyneuropathy.

In various embodiments, the dose of anti-CD30 antibody drug conjugate is delayed by one week, or two weeks, if peripheral neuropathy appears, and therapy is continued when the neuropathy is resolved or determined to be Grade 2 or less or Grade 1 or less.

Neutropenia

Neutropenia is a common side effect of chemotherapy regimens and results from depletion of neutrophils in the blood of patients receiving chemotherapeutic treatment. Neutropenia is also observed in treatment with brentuximab vedotin. Neutropenia is commonly diagnosed based on levels of neutrophils in the blood. For example, Grade 3 neutropenia refers to an absolute blood neutrophil count [ANC]<$1.0 \times 10^9$/l); Grade 4 neutropenia refers to absolute blood neutrophil count [ANC]<$0.5 \times 10^9$/l), Febrile neutropenia refers to neutropenia with fever, the subject having a single oral temperature 38.3° C. or 38.0° C. for >1 h, with grade 3/4 neutropenia.

It is contemplated herein that subjects receiving an anti-CD30 antibody drug conjugate, e.g., brentuximab vedotin, or anti-CD30 antibody drug conjugate in combination with chemotherapy, such as AVD combination therapy, receive granulopoiesis stimulating factors prophylactically beginning with cycle 1 of the administration of the anti-CD30 antibody drug conjugate, e.g., as primary prophylaxis. Exemplary granulopoiesis stimulating factors include granulocyte colony stimulating factor (GCSF), derivatives of GCSF, or granulocyte monocyte colony stimulating factor (GMCSF). Commercially available GCSF contemplated for use herein are filgrastim (NEUPOGEN®) and pegfilgrastim (NEULASTA®). Commercially available GMCSF is available as sargramostim (LEUKINE®).

Provided herein is a method for treating a hematologic cancer in a subject comprising administering an anti-CD30 antibody drug conjugate and prophylactically administering a granulopoiesis stimulating factor beginning with cycle 1 of the administration of the anti-CD30 antibody drug conjugate, wherein the granulopoiesis stimulating factor is administered within 1 day to within 7 days after beginning with cycle 1 of the administration of the anti-CD30 antibody drug conjugate. In further embodiments, the granulopoiesis stimulating factor is administered from within 1 day or 2 days to within 5 days after beginning with cycle 1 of the administration of the anti-CD30 antibody drug conjugate. In various embodiments, the granulopoiesis stimulating factor is administered about 24 hours to about 36 hours after each administration of anti-CD30 antibody drug conjugate, optionally anti-CD30 antibody drug conjugate in combination with a chemotherapy regimen described herein. In various embodiments, the granulopoiesis stimulating factor is administered 24 hours to 36 hours after each administration of, i.e., after each dose of, anti-CD30 antibody drug conjugate.

In some embodiments, the method is a method for decreasing adverse events associated with anti-CD30 antibody drug conjugate administration, e.g. neutropenia, febrile neutropenia, incidence of infection, pyrexia, gastrointestinal disorders such as constipation, vomiting, diarrhea, stomatitis, abdominal pain, nervous system disorders such as peripheral sensory neuropathy, peripheral motor neuropathy, musculoskeletal disorders such as bone pain, back pain, respiratory disorders such as dyspnea, and other adverse events such as decreased weight, increased alanine aminotransferase, decreased appetite and/or insomnia. In some embodiments, the method is a method for decreasing neutropenia and/or febrile neutropenia and/or incidence of infection associated with anti-CD30 antibody drug conjugate administration.

Also provided is a method for decreasing the incidence of infection in a subject receiving an the anti-CD30 antibody drug conjugate comprising administering to the subject granulopoiesis stimulating factor in an amount effective to reduce infections, wherein the granulopoiesis stimulating factor is administered from 1 day to 7 days after beginning with cycle 1 of the administration of the anti-CD30 antibody drug conjugate. The granulopoiesis stimulating factor may also be administered from 1 day to 7 days, or 1 day or 2 days to 5 days, after beginning with cycle 1 of the administration of the anti-CD30 antibody drug conjugate. In various embodiments, the granulopoiesis stimulating factor is administered about 24 hours to about 36 hours after each administration of anti-CD30 antibody drug conjugate, optionally anti-CD30 antibody drug conjugate in combination with a chemotherapy regimen described herein. In various embodiments, the granulopoiesis stimulating factor is administered 24 hours to 36 hours after each administration of anti-CD30 antibody drug conjugate.

Also contemplated is a method for reducing the incidence of neutropenia and/or febrile neutropenia in a subject receiving treatment with an anti-CD30 antibody drug conjugate comprising administering to the subject a granulopoiesis stimulating factor, wherein the stimulating factor is administered from 1 day to 7 days beginning with cycle 1 of the administration of the anti-CD30 antibody drug conjugate, optionally from 1 day or 2 days to 5 days after beginning with cycle 1 of the administration of the anti-CD30 antibody drug conjugate. In various embodiments, the subject has febrile neutropenia and is 60 years old or older. In various embodiments, the granulopoiesis stimulating factor is administered about 24 hours to about 36 hours after each administration of anti-CD30 antibody drug conjugate, optionally anti-CD30 antibody drug conjugate in combination with a chemotherapy regimen described herein. In various embodiments, the granulopoiesis stimulating factor is administered 24 hours to 36 hours after each administration of anti-CD30 antibody drug conjugate.

Further contemplated is a method wherein the granulopoiesis stimulating factor is administered from 1 day to 7 days after a second, or subsequent, administration of anti-CD30 antibody drug conjugate. In certain embodiments, the granulopoiesis stimulating factor is administered from 1 day or 2 days to 5 days after the second or subsequent administration of anti-CD30 antibody drug conjugate. In various embodiments, the granulopoiesis stimulating factor is administered about 24 hours to about 36 hours after each administration of anti-CD30 antibody drug conjugate, optionally anti-CD30 antibody drug conjugate in combination with a chemotherapy regimen described herein. In various embodiments, the granulopoiesis stimulating factor is administered 24 hours to 36 hours after each administration of anti-CD30 antibody drug conjugate.

In various embodiments, the subject that has not received anti-CD30 antibody drug conjugate therapy previously. In various embodiments, the subject has not experienced treatment-emergent Grade 3-4 neutropenia after anti-CD30 antibody drug conjugate administration.

It is contemplated that the granulopoiesis stimulating factor is granulocyte colony stimulating factor (GCSF). It is contemplated that the GCSF is a long-acting GCSF or not a long acting GCSF.

In various embodiments, when the stimulating factor is not long-acting GCSF, e.g. filgrastim, it can be administered starting from 1 to 7 days, from 1 to 5 days, or 1 to 3 days after beginning with cycle 1 of the administration of the anti-CD30 antibody drug conjugate, e.g. in daily doses. In certain embodiments, the GCSF is administered on day 2, 3, 4, 5, 6 and/or 7 after anti-CD30 antibody drug conjugate or A+AVD therapy. In various embodiments, the filgrastim is administered at a dose of 5 ug/kg/day to 10 ug/kg/day for the duration of at least 3, 4, 5, 6, 7, 8, 9, 10, 11, 12, 13 or 14 days.

Pegfilgrastim is a long-lasting, PEGylated form of filgrastim that has a longer half-life in vivo. In various embodiments, pegfilgrastim is administered at 6 mg/dose from 1 day to 5 days after anti-CD30 antibody drug conjugate treatment, or optionally after A+AVD therapy. In certain embodiments, the GCSF is administered in a single dose, or a multiple dose on the same day, on day 2, day 3, day 4 or day 5 after anti-CD30 antibody drug conjugate or A+AVD therapy. In various embodiments, the GCSF is administered about 24 hours to about 36 hours after each administration of anti-CD30 antibody drug conjugate, optionally anti-CD30 antibody drug conjugate in combination with a chemotherapy regimen described herein. In various embodiments, the G-CSF is administered 24 hours to 36 hours after each administration of anti-CD30 antibody drug conjugate.

In various embodiments, the granulopoiesis stimulating factor is administered intravenously or subcutaneously. It is contemplated that the granulopoiesis stimulating factor is given in a single dose or multiple doses, e.g., in multiple daily doses.

It is contemplated that a subject receiving a granulopoiesis stimulating factor and anti-CD30 antibody drug conjugate may also be administered an antibiotic to address issues of febrile neutropenia and/or infection. Exemplary antibiotics contemplated include those known in the art, such as cephalosporin, sulfamethoxazole-trimethoprim, ACYCOLOVIR®, FLUCANOZOLE®, or INTRACONAZOLE®.

In various embodiments, the anti-CD30 antibody drug conjugate is administered every 3 weeks. In various embodiments, if the subject is receiving 1.8 mg/kg of anti-CD30 antibody drug conjugate every three weeks, the dose may be reduced to 1.2 mg/kg up to a maximum of 120 mg every two weeks to improve neutropenia, e.g., Grade 4 neutropenia.

In various embodiments, the anti-CD30 antibody drug conjugate is administered every 2 weeks, e.g., on days 1 and 15 of a 28 day cycle. In various embodiments, the anti-CD30 antibody drug conjugate is administered for no more than six cycles. In various embodiments, the anti-CD30 antibody drug conjugate is administered for four to six cycles. Optionally, when the anti-CD30 antibody drug conjugate is administered every 2 weeks, the regimen further comprises administering a chemotherapy consisting essentially of doxorubicin, vinblastine, and dacarbazine (AVD) as a combination therapy, on the same day as the anti-CD30 antibody therapy.

In various embodiments, the hematologic cancer is selected from the group consisting of classical Hodgkin Lymphoma, non-Hodgkin Lymphoma, cutaneous T-cell lymphoma (CTCL), and anaplastic large cell lymphoma (ALCL).

In various embodiments, the hematologic cancer is classical Hodgkin Lymphoma. In various embodiments, the hematologic cancer is a stage III or IV classical Hodgkin Lymphoma. In various embodiments, the hematologic cancer of the subject has not been treated.

In various embodiments, the anaplastic large cell lymphoma (ALCL) is a systemic anaplastic large cell lymphoma (sALCL).

In various embodiments, the cutaneous T-cell lymphoma (CTCL) is a mycosis fungoides (MF). In various embodiments, the mycosis fungoides (MF) is a CD30-positive mycosis fungoides (MF). In various embodiments, the cutaneous T-cell lymphoma (CTCL) is a primary cutaneous anaplastic large cell lymphoma (pcALCL).

In various embodiments, the subject has received prior systemic therapy or prior radiation In various embodiments, a subject with mycosis fungoides or primary cutaneous anaplastic large cell lymphoma is administered therapy comprising an anti-CD30 antibody drug conjugate at a dose of 1.8 mg/kg every three weeks.

It is further contemplated that upon completion of therapy with anti-CD30 antibody drug conjugate as described herein, optionally in combination with a chemotherapy regimen, the subject may receive an additional treatment to address one or more symptoms of cancer that remains at the end of treatment, or may be refractory to the therapy herein. Such treatments include, but are not limited to surgery, radiation therapy, proton beam therapy, stem cell transplant, and/or additional chemotherapeutic regimens.

Formulations

Various delivery systems can be used to administer antibody-drug conjugates. In certain preferred embodiments of the present invention, administration of the antibody-drug conjugate compound is by intravenous infusion. In some embodiments, administration is by a 30 minute, 1 hour or two hour intravenous infusion.

The antibody-drug conjugate compound can be administered as a pharmaceutical composition comprising one or more pharmaceutically compatible ingredients. For example, the pharmaceutical composition typically includes one or more pharmaceutically acceptable carriers, for example, water-based carriers (e.g., sterile liquids). Water is a more typical carrier when the pharmaceutical composition is administered intravenously.

The composition, if desired, can also contain, for example, saline salts, buffers, salts, nonionic detergents, and/or sugars. Examples of suitable pharmaceutical carriers are described in "Remington's Pharmaceutical Sciences" by E. W. Martin. The formulations correspond to the mode of administration.

The present disclosure provides, for example, pharmaceutical compositions comprising a therapeutically effective amount of the antibody-drug conjugate, a buffering agent, optionally a cryoprotectant, optionally a bulking agent, optionally a salt, and optionally a surfactant. Additional agents can be added to the composition. A single agent can serve multiple functions. For example, a sugar, such as trehalose, can act as both a cryoprotectant and a bulking agent. Any suitable pharmaceutically acceptable buffering agents, surfactants, cyroprotectants and bulking agents can be used in accordance with the present invention.

In addition to providing methods for treating a hematological cancer, the present invention provides antibody drug conjugate formulations including drug conjugate formulations that have undergone lyophilization, or other methods of protein preservation, as well as antibody drug formulations that have not undergone lyophilization.

In some embodiments, the antibody drug conjugate formulation comprises (i) about 1-25 mg/ml, about 3 to about 10 mg/ml of an antibody-drug conjugate, or about 5 mg/ml (e.g., an antibody-drug conjugate of formula I or a pharmaceutically acceptable salt thereof), (ii) about 5-50 mM, preferably about 10 mM to about 25 mM of a buffer selected from a citrate, phosphate, or histidine buffer or combinations thereof, preferably sodium citrate, potassium phosphate, histidine, histidine hydrochloride, or combinations thereof, (iii) about 3% to about 10% sucrose or trehalose or combinations thereof, (iv) optionally about 0.05 to 2 mg/ml of a surfactant selected from polysorbate 20 or polysorbate 80 or combinations thereof; and (v) water, wherein the pH of the composition is from about 5.3 to about 7, preferably about 6.6.

In some embodiments, an antibody drug conjugate formulation will comprise about 1-25 mg/ml, about 3 to about 10 mg/ml, preferably about 5 mg/ml of an antibody-drug conjugate, (ii) about 10 mM to about 25 mM of a buffer selected from sodium citrate, potassium phosphate, histidine, histidine hydrochloride or combinations thereof, (iii) about 3% to about 7% trehalose or sucrose or combinations thereof, optionally (iv) about 0.05 to about 1 mg/ml of a surfactant selected from polysorbate 20 or polysorbate 80, and (v) water, wherein the pH of the composition is from about 5.3 to about 7, preferably about 6.6.

In some embodiments, an antibody drug conjugate formulation will comprise about 5 mg/ml of an antibody-drug conjugate, (ii) about 10 mM to about 25 mM of a buffer selected from sodium citrate, potassium phosphate, histidine, histidine hydrochloride or combinations thereof, (iii) about 3% to about 7% trehalose, optionally (iv) about 0.05 to about 1 mg/ml of a surfactant selected from polysorbate 20 or polysorbate 80, and (v) water, wherein the pH of the composition is from about 5.3 to about 7, preferably about 6.6.

Any of the formulations described above can be stored in a liquid or frozen form and can be optionally subjected to a preservation process. In some embodiments, the formulations described above are lyophilized, i.e., they are subjected to lyophilization. In some embodiments, the formulations described above are subjected to a preservation process, for example, lyophilization, and are subsequently reconstituted with a suitable liquid, for example, water. By lyophilized it is meant that the composition has been freeze-dried under a vacuum. Lyophilization typically is accomplished by freezing a particular formulation such that the solutes are separated from the solvent(s). The solvent is then removed by sublimation (i.e., primary drying) and next by desorption (i.e., secondary drying).

The formulations of the present invention can be used with the methods described herein or with other methods for treating disease. The antibody drug conjugate formulations may be further diluted before administration to a subject. In some embodiments, the formulations will be diluted with saline and held in IV bags or syringes before administration to a subject. Accordingly, in some embodiments, the methods for treating a hematologic cancer in a subject will comprise administering to a subject in need thereof a weekly dose of a pharmaceutical composition comprising antibody-drug conjugates having formula I wherein the administered dose of antibody-drug conjugates is from about 1.8 mg/kg or 1.2 mg/kg of the subject's body weight to 0.9 mg/kg of the subject's body weight and the pharmaceutical composition is administered for at least three weeks and wherein the antibody drug conjugates, prior to administration to a subject, were present in a formulation comprising (i) about 1-25 mg/ml, preferably about 3 to about 10 mg/ml of the antibody-drug conjugate (ii) about 5-50 mM, preferably about 10 mM to about 25 mM of a buffer selected from sodium citrate, potassium phosphate, histidine, histidine hydrochloride, or combinations thereof, (iii) about 3% to about 10% sucrose or trehalose or combinations thereof, (iv) optionally about 0.05 to 2 mg/ml of a surfactant selected from polysorbate 20 or polysorbate 80 or combinations thereof; and (v) water, wherein the pH of the composition is from about 5.3 to about 7, preferably about 6.6.

Formulations of chemotherapeutics contemplated for use herein, including doxorubicin, vinblastine, and dacarbazine are provided as typically used in the treatment of cancers. For example, doxorubicin, vinblastine, and dacarbazine are commercially available and approved by the United States FDA and other regulatory agencies for use in treating patients with multiple types of cancer.

The present invention also provides kits for the treatment of a hematologic cancer. The kit can comprise (a) a container containing the antibody-drug conjugate and optionally, containers comprising one or more of doxorubicin, vinblastine, or dacarbazine. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

EXAMPLES

Example 1

This open-label, multicenter, phase 3 trial randomized patients with previously untreated stage III/IV classical Hodgkin lymphoma to receive brentuximab vedotin, doxorubicin, vinblastine, dacarbazine (A+AVD; n=664) or doxorubicin, bleomycin, vinblastine, dacarbazine (ABVD; n=670). The primary endpoint was modified progression-free survival (PFS) per independent review facility and key secondary endpoint, overall survival.
Materials and Methods
TRIAL DESIGN: Patients were randomized 1:1 to receive A+AVD (brentuximab vedotin 1.2 mg/kg, doxorubicin 25 mg/m$^2$, vinblastine 6 mg/m$^2$, dacarbazine 375 mg/m$^2$) or ABVD (doxorubicin 25 mg/m$^2$, bleomycin 10 units/m$^2$, vinblastine 6 mg/m$^2$, dacarbazine 375 mg/m$^2$) intravenously on days 1 and 15 of each 28-day cycle for up to 6 cycles. Brentuximab vedotin was administered over 30 minutes, starting within approximately 1 hour after completion of AVD. Dose reductions/modifications are described in FIG. 7. Patients were stratified by region (Americas vs. Europe vs. Asia) and International Prognostic Score (IPS)15 (0-1 vs. 2-3 vs. 4-7). End-of-Cycle-2 PET (PET2) results guided an optional switch to alternative frontline therapy at the treating physician's discretion for patients with a Deauville score[16] of 5.

PATIENTS: Patients (≥18 years of age) with histologically confirmed advanced (Ann Arbor stage III/IV)17 classical Hodgkin lymphoma according to the World Health Organisation Classification,18 not previously treated with systemic chemotherapy/radiotherapy, were eligible. Patients were required to have an Eastern Cooperative Oncology Group performance status ≤2,[19] and satisfactory absolute neutrophil and platelet counts, hemoglobin levels, and liver and kidney function marker levels (except for patients with involvement of the marrow or liver or Gilbert syndrome). Patients with nodular lymphocyte-predominant Hodgkin lymphoma were ineligible, as were those with peripheral sensory/motor neuropathy, a positive pregnancy test, known cerebral/meningeal disease, any evidence of residual disease from another malignancy or diagnosis of another malignancy within 3 years before the first dose, or clinically relevant cardiovascular conditions.

ENDPOINTS: The primary endpoint was modified progression-free survival (PFS), defined as time to progression, death, or evidence of non-CR after completion of frontline therapy per independent review facility (IRF) followed by subsequent anticancer therapy. Timing of the modified event was the date of the first PET scan post-completion of frontline therapy demonstrating the absence of CR, defined as Deauville score of ≥3. In the absence of disease progression a switch to an alternative frontline therapy, for any reason, prior to completion of treatment with the randomized regimen was not considered an event.

The key secondary endpoint was overall survival (OS), defined as time from randomization to death due to any cause.

ASSESSMENTS: Response and progression were evaluated according to the Revised Response Criteria for Malignant Lymphomas.[20] Computed tomography scans were performed at screening, after Cycle 2, after the last dose of frontline therapy and, during the follow-up period, every 3 months for the first year and 6 months thereafter. PET scans were conducted at the end of Cycle 2 and end of treatment.

Safety was evaluated by the incidence of adverse events, using the Medical Dictionary for Regulatory Activities (MedDRA; v19.0), and National Cancer Institute Common Terminology Criteria for Adverse Events v4.03, and by changes in vital signs, and clinical laboratory results.

STATISTICAL ANALYSIS: Statistical calculations estimated 260 modified PFS events were required to detect a hazard ratio (HR) of 0.67 with 90% power at a 1 sided significance level of 0.025. The study is powered on the following assumption: a 2-year modified PFS of 81% for patients in the A+AVD arm and 73% for patients in the ABVD arm. Approximately 1240 patients were planned to be randomized to achieve (with 95% probability) 260 modified PFS events. The primary endpoint was summarized by the Kaplan-Meier method and evaluated using a stratified log-rank test. A stratified Cox regression model was used to estimate the HR and the 95% confidence interval (CI) for the treatment effect. The stratification factors included region and IPS score at baseline. The OS interim analysis was to be performed (1-sided 0.025 level) if the primary endpoint test was statistically significant. The final OS analysis will be performed when 112 deaths have occurred. Overall type I error for the OS analysis will be controlled using the O'Brien Fleming method with a Lan DeMets alpha spending function.

All efficacy evaluations were conducted using the intent-to-treat population unless otherwise specified. Safety was analyzed in patients who received at least one dose of study drug (safety population).

Results 1334 patients at 218 sites in 21 countries underwent randomization to receive A+AVD (n=664) or ABVD (n=670) (intent-to-treat population). Overall, 58% of patients were male, 64% had stage IV disease, 62% had extranodal involvement at diagnosis, 58% had B symptoms, and median age was 36 years (34% of patients 45 years). Baseline characteristics were generally well balanced between the two groups [FIG. 2 (Table 1)].

After a median follow-up of 24.9 months (range, 0.0 to 49.3), there was a statistically significant difference in the primary endpoint of modified PFS per IRF in favor of A+AVD versus ABVD (2-year modified PFS rate 82.1% [95% CI, 78.7 to 85.0] versus 77.2% [95% CI, 73.7 to 80.4] for A+AVD and ABVD, respectively) (HR, 0.770; 95% CI, 0.603 to 0.982; P=0.035), corresponding to a 23% risk reduction, with 117 events in the A+AVD arm and 146 in the ABVD arm (FIG. 1A). Modified PFS events consisted of disease progression (90 vs. 102), death due to any cause (18 vs. 22), or receipt of subsequent anticancer therapy for after failing to achieve a CR at the completion of frontline therapy (9 vs. 22) in A+AVD and ABVD arms, respectively [FIG. 3 (Table 2)]. The majority (71%) of subsequent anticancer therapies consisted of salvage chemotherapy (7/9 A+AVD; 15/22 ABVD), with radiotherapy given to the remainder in both arms (FIG. 8). Most events were associated with an end-of-treatment PET scan Deauville score 4 or 5 and met criteria for a progression event per investigator.

For investigator-determined modified PFS, the HR was 0.725 (95% CI, 0.574 to 0.916; P=0.007; FIG. 1B). There was 91% concordance between IRF and investigator determination of a modified PFS event. By investigator assessment, the 2-year modified PFS event rate was 81.0% (95% CI, 77.6 to 83.9) with A+AVD versus 74.4% (95% CI, 70.7 to 77.7) with ABVD.

Pre-specified subgroup analyses of modified PFS showed a HR<1 for A+AVD versus ABVD in the majority of subgroups (FIG. 10). Certain subgroups of patients appeared to benefit more with A+AVD versus ABVD (patients from North America; patients with involvement of >1 extranodal site; patients with IPS 4-7; males; patients with stage IV disease; patients aged <60 years). The PET2-negativity rate (Deauville score 1-3) was 89% with A+AVD versus 86% with ABVD.

Figure 6:
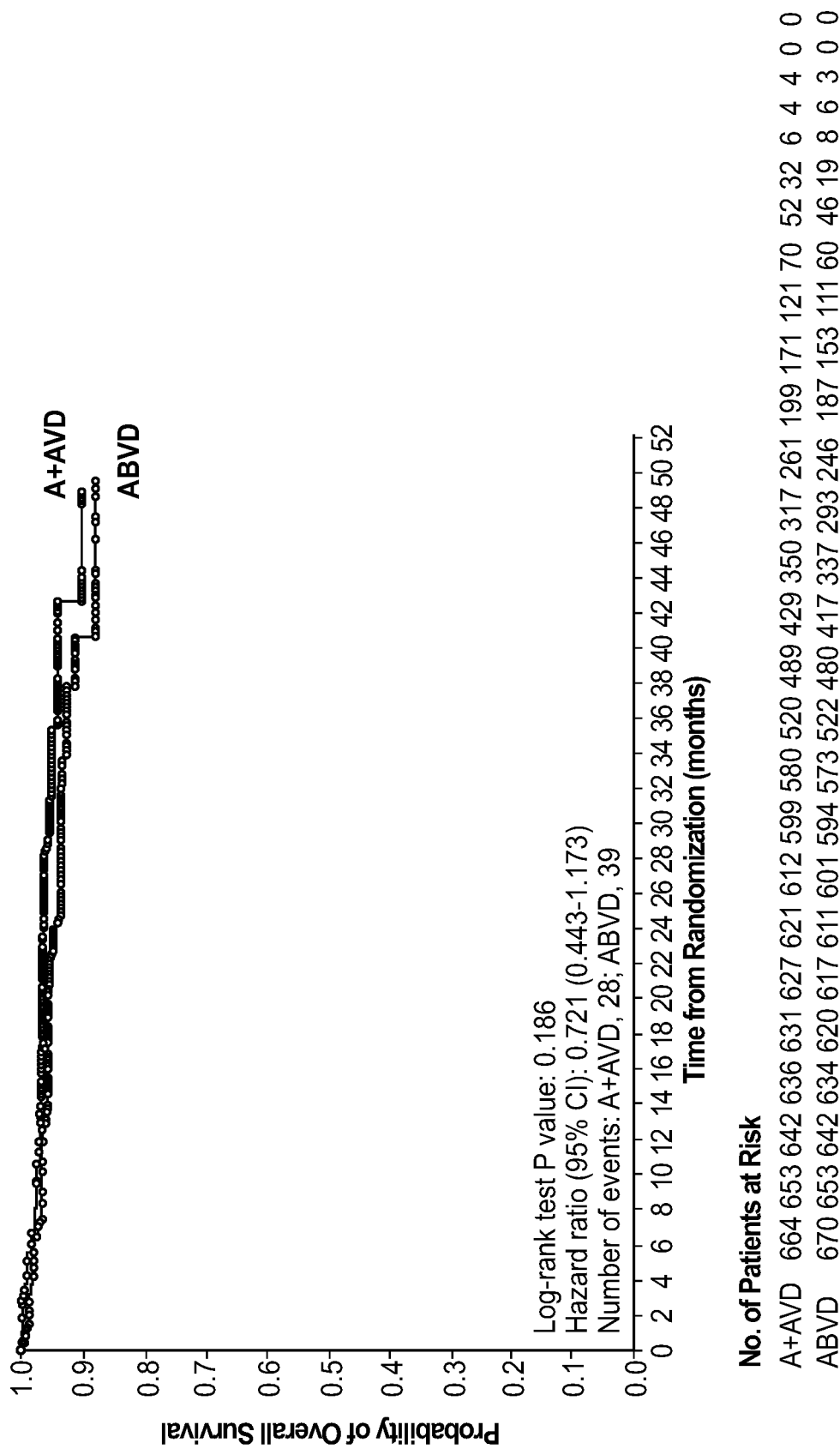
FIG. 6. Kaplan-Meier Analysis of Overall Survival in the Intent-to-treat Population.

There were 28 deaths in the A+AVD arm (9 on study [within 30 days of the last dose of frontline therapy] and 19 during follow-up [after 30 days of the last dose of frontline therapy]) and 39 in the ABVD arm (13 on-study, 26 during follow-up). The interim OS HR was 0.721 (95% CI, 0.443 to 1.173; P=0.186) in favor of A+AVD versus ABVD (FIG. 6). Other secondary endpoints are shown in FIG. 4 (Table 3). Only 15/662 patients randomized to A+AVD and 9/659 randomized to ABVD switched to alternative chemotherapy during frontline therapy for reasons other than progressive disease (Deauville score assessment of 5 in 1/15 and 4/9 patients, adverse events in 12/15 and 1/9 patients, and other reasons in 2/15 and 4/9, respectively) (FIG. 9).

Overall, fewer patients on the A+AVD arm received subsequent anticancer therapies. Therapies in the A+AVD and ABVD arms, respectively, were radiation (each n=52), chemotherapy (n=66 vs n=99), high-dose chemotherapy plus transplant (n=36 vs n=54), immunotherapy (n=10 vs n=16), and chemotherapy plus radiation (n=2 vs n=3).

Median duration of treatment and number of completed cycles were similar across arms (FIG. 10). The proportions of patients receiving the individual regimen agents as intended, without dose modification such as delays/holds/reductions, are shown in FIG. 10.

The safety profiles of both arms are summarized in FIG. 5 (Table 4). Overall, neutropenia was reported in 58% of patients receiving A+AVD and 45% receiving ABVD, and febrile neutropenia in 19% and 8%, respectively. In both arms, the incidence of febrile neutropenia was higher in patients aged ≥60 versus <60 years (A+AVD: 37% vs. 17%, and ABVD: 17% vs. 6%, respectively), and in earlier versus later cycles of therapy (A+AVD: 9% in Cycle 1 vs. 1-6% cumulatively in Cycles 2-6, and ABVD: 4% in Cycle 1 vs. ≤1% in Cycles 2-6, respectively). The incidence of study drug discontinuations due to neutropenia or febrile neutropenia was ≤1% in both arms.

The rate of infections (determined by the MedDRA primary system organ class term of 'Infections and infestations') was 55% (361/662) in the A+AVD arm and 50% (331/659) in the ABVD arm; Grade infection rates were 18% (116/662) and 10% (66/659), respectively. Discussion with the Independent Data Monitoring Committee (after 76% enrollment completion) led to the recommendation of granulocyte colony-stimulating factor (G-CSF) primary prophylaxis for newly randomized patients receiving A+AVD based on a higher incidence of febrile neutropenia. In the A+AVD arm, among all patients given G-CSF primary prophylaxis (defined as G-CSF use by Day 5 of study treatment; n=83), there was a reduced incidence of febrile neutropenia (from 21% [119/579] to 11% [9/83]) and occurrence of Grade infections and infestations (from 18% [107/579] to 11% [9/83]).

Peripheral neuropathy (determined by a protocol-specified standardized MedDRA query [SMQ]; FIG. 11) occurred in 67% (442/662) of patients receiving A+AVD and 43% (286/659) receiving ABVD: Grade in 11% (70/662) of patients in the A+AVD arm (Grade 4 in 1 patient) versus 2% (11/659) of patients in the ABVD arm and leading to study drug discontinuations in 10% (44/442) versus 4% (11/286), respectively. Two-thirds of patients (295/442) experiencing peripheral neuropathy in the A+AVD arm had resolution or improvement (by grade) of peripheral neuropathy events at last follow-up; 92% of ongoing peripheral neuropathy events at last follow-up were Grade 1 (64%) or 2 (29%) in the A+AVD arm. Pulmonary toxicity, as defined in Interstitial Lung Disease (SMQ) events, was reported in 12/662 (2%) patients in the A+AVD arm versus 44/659 (7%) in the ABVD arm; Grade events were reported in 5/662 [<1%] versus 21/659 [3%] patients, respectively.

There were nine on-study deaths in the A+AVD arm and 13 in the ABVD arm. In the A+AVD arm, 7/9 deaths were associated with neutropenia (all occurred in patients who had not received G-CSF primary prophylaxis before the onset of neutropenia) and 2 were due to myocardial infarction. Of 13 on-study deaths in the ABVD arm, 11 were due to, or associated with, pulmonary-related toxicity, one was due to pneumonia/cardiac arrest and 1 cause was unknown.

The large, international, randomized phase 3 ECHELON-1 trial in newly diagnosed patients with stage III/IV classical Hodgkin lymphoma showed a statistically significant and clinically meaningful improvement in modified PFS with brentuximab vedotin plus AVD compared with the treatment standard, ABVD, corresponding to a 23% reduction in failure of the primary chemotherapy treatment as measured by the IRF and a 28% reduction as measured by the trial investigators. A+AVD is the first regimen in frontline Hodgkin lymphoma to show superior outcomes when compared to ABVD while eliminating exposure to bleomycin.

The goal of frontline chemotherapy for Hodgkin lymphoma is to cure patients without the need for additional therapy. As metabolically detectable residual disease reliably predicts imminent progression, it is accepted practice to initiate subsequent chemotherapy/radiotherapy based on a PET-positive scan at the end of frontline treatment.[21-23] In this setting, the conventional endpoint of PFS does not accurately assess the curative intent of frontline chemotherapy. Thus, in ECHELON-1, the primary endpoint was 'modified' PFS, which, in addition to disease progression or death, includes evidence of non-CR after completion of frontline chemotherapy (based on PET results per IRF) followed by subsequent anticancer therapy as an event, thus accurately assessing the curative potential of the frontline chemotherapy.

Results of the interim analysis of OS, the key secondary endpoint, and all other secondary efficacy endpoints trended in favor of A+AVD, further supporting the conclusion that A+AVD is a more effective frontline treatment for advanced Hodgkin lymphoma than ABVD. Furthermore, the benefit of A+AVD was observed consistently in the majority of pre-specified subgroups, including patients with involvement of >1 extranodal site and IPS 4-7. PET2-positivity rate in ECHELON-1 was low, and there was a higher proportion of PET2-negative patients in the A+AVD arm compared with the ABVD arm.

Adverse events were consistent with the individual regimen components. The nature of the lung toxicity of bleomycin, which resulted in the majority of on-study deaths in the ABVD arm, is unpredictable, and the only approach known to mitigate the risk of adverse pulmonary events is to discontinue bleomycin. In the response-adapted approach adopted by the RATHL study, omission of bleomycin from ABVD after 2 cycles and negative findings on interim PET resulted in a lower incidence of pulmonary toxic effects than with continued ABVD without significantly lower efficacy.[8] ECHELON-1 demonstrates that the addition of brentuximab vedotin and the elimination of bleomycin from frontline therapy in the A+AVD regimen lowers the incidence of pulmonary toxicity while improving efficacy compared with ABVD. With A+AVD, there were no new safety risks identified, although the incidence of febrile neutropenia was higher than expected and there was an increased incidence of infections in the A+AVD arm. The majority of the on-study deaths were associated with febrile neutropenia; however, primary prophylaxis with G CSF appeared to mitigate the increased risk of febrile neutropenia and its associated sequelae in the subgroup of 83 patients who received primary prophylaxis, resulting in rates of neutropenia, febrile neutropenia, and serious infection that were similar to the ABVD arm. One-third fewer patients treated with A+AVD received subsequent salvage chemotherapy and high-dose chemotherapy and transplant compared with those treated with ABVD and were therefore less likely to experience the toxicities associated with aggressive salvage therapies.

The results of ECHELON-1 are particularly important considering the opportunity A+AVD provides to administer potentially curative treatment safely to older patients, a special group considering their disease incidence (~20% of all cases), known lower treatment efficacy rates, and typically higher rates of severe toxicity, especially pulmonary toxicity associated with bleomycin.[6,24,25] It is also important to consider the lifetime burden of late and long-term adverse effects from salvage chemotherapy, radiotherapy, and ASCT (including infertility, pulmonary and cardiac toxicities, and secondary malignancies) when choosing frontline patient management.[26,27] ECHELON-1 verifies that brentuximab vedotin in combination with AVD is more effective than ABVD for the frontline treatment of advanced-stage classical Hodgkin lymphoma and has a manageable toxicity profile, establishing A+AVD as a new frontline standard of care.

Example 2

In a follow up to the ECHELON-1 trial, a further study investigating the impact of G-CSF primary prophylaxis for advanced stage HL patients as set out in the above Example is undertaken. Treated patients are at least 18 years of age, and are treatment-naive HL patients with Ann Arbor Stage 3 or 4 disease. The subjects are histologically confirmed classical HL according to the current World Health Organization (WHO) Classification and exhibit bidimensional measureable disease as documented by radiographic technique. Subjects are excluded if any of the following criteria are met: nodular lymphocyte predominant HL, history of another malignancy within 2 years of the first dose of study, drug or any evidence of residual disease from a previously diagnosed malignancy; patients with nonmelanoma skin cancer, localized prostate cancer, or carcinoma in situ of any type are not excluded if they have undergone complete resection; prior immunosuppressive chemotherapy, therapeutic radiation, or any immunotherapy within 12 weeks of the first study drug dose; active cerebral/meningeal disease related to the underlying malignancy; any active Grade 3 or higher viral, bacterial, or fungal infection within two weeks of the first dose of study drug (Grade 3 defined by the National Cancer Institute's Common Terminology Criteria for Adverse Events, NCI CTCAE Version 4.03); current therapy with other systemic anti-neoplastic or investigational agents; grade 3 or higher pulmonary disease unrelated to underlying malignancy; history of a cerebral vascular event within 6 months of first dose of study drug; Child-Pugh B or C hepatic impairment; any peripheral sensory or motor neuropathy; patients who are pregnant or breastfeeding; other serious condition that would impair the patient's ability to receive or tolerate the planned treatment and follow-up.

Patients are administered A+AVD therapy in combination with G-CSF, wherein the G-CSF is administered 24 to 36 hours after every cycle of A+AVD (brentuximab vedotin 1.2 mg/kg, doxorubicin 25 mg/m$^2$, vinblastine 6 mg/m$^2$, dacarbazine 375 mg/m$^2$) therapy for 6 cycles of treatment (12 doses, days 1 and 15 of each 28 day cycle). Primary endpoints evaluated include whether the drug combination reduces the number of patients who experience the side effect of febrile neutropenia, efficacy, and dose intensity in patients. Secondary endpoints include analysis of primary refractory response rate, complete response rate, progression free survival, subsequent anticancer therapy utilization rate, mean dose intensity and rate of dose reduction and delays.

It is predicted that administration of G-CSF following the regimen herein, e.g., prophylactic administration of G-CSF given 24-36 hours after each dose/administration of anti-CD30 antibody drug conjugate combination therapy, will reduce incidence of febrile neutropenia and occurrence of Grade infections and infestations in patients A+AVD therapy.

Numerous modifications and variations of the invention as set forth in the above illustrative examples are expected to occur to those skilled in the art. Consequently only such limitations as appear in the appended claims should be placed on the invention.

REFERENCES

1. Engert A. ABVD or BEACOPP for Advanced Hodgkin Lymphoma. J Clin Oncol 2016; 34:1167-9.
2. Canellos G P, Anderson J R, Propert K J, et al. Chemotherapy of advanced Hodgkin's disease with MOPP, ABVD, or MOPP alternating with ABVD. N Engl J Med 1992; 327:1478-84.
3. Carde P, Karrasch M, Fortpied C, et al. Eight Cycles of ABVD Versus Four Cycles of BEACOPPescalated Plus Four Cycles of BEACOPPbaseline in Stage III to IV, International Prognostic Score>1=3, High-Risk Hodgkin Lymphoma: First Results of the Phase III EORTC 20012 Intergroup Trial. J Clin Oncol 2016; 34:2028-36.
4. Gordon L I, Hong F, Fisher R I, et al. Randomized phase III trial of ABVD versus Stanford V with or without radiation therapy in locally extensive and advanced-stage Hodgkin lymphoma: an intergroup study coordinated by the Eastern Cooperative Oncology Group (E2496). J Clin Oncol 2013; 31:684-91.
5. Canellos G P, Duggan D, Johnson J, Niedzwiecki D. How important is bleomycin in the adriamycin+bleomycin+vinblastine+dacarbazine regimen? J Clin Oncol 2004; 22:1532-3.
6. Martin W G, Ristow K M, Habermann T M, Colgan J P, Witzig T E, Ansell S M. Bleomycin pulmonary toxicity has a negative impact on the outcome of patients with Hodgkin's lymphoma. J Clin Oncol 2005; 23:7614-20.
7. Borchmann P, Goergen H, Kobe C, et al. Treatment Reduction in Patients with Advanced-Stage Hodgkin Lymphoma and Negative Interim PET: Final Results of the International, Randomized Phase 3 Trial HD18 by the German Hodgkin Study Group. Presented at the 22nd Annual Meeting of the European Hematology Association, Madrid, Spain, Jun. 22-25, 2017. Haematologica 2017; 102: Abstract S150.
8. Johnson P, Federico M, Kirkwood A, et al. Adapted Treatment Guided by Interim PET-CT Scan in Advanced Hodgkin's Lymphoma. N Engl J Med 2016; 374:2419-29.
9. Borchmann P, Eichenauer D A, Pluetschow A, et al. Targeted Beacopp Variants in Patients with Newly Diagnosed Advanced Stage Classical Hodgkin Lymphoma: Final Analysis of a Randomized Phase II Study. Presented at the 57th Annual Meeting of the American Society of Hematology, Orlando, Fla., Dec. 5-8, 2015. Blood 2015; 126.
10. Schwab U, Stein H, Gerdes J, et al. Production of a monoclonal antibody specific for Hodgkin and Sternberg-Reed cells of Hodgkin's disease and a subset of normal lymphoid cells. Nature 1982; 299:65-7.
11. ADCETRIS® (brentuximab vedotin) US Prescribing Information. Available at: http://www.seattlegenetics/com/application/files/9414/7621/9892/adcetris_UPSI.pdf [Last accessed 10 Aug. 2017].
12. ADCETRIS® (brentuximab vedotin) EU Summary of Product Characteristics. Available at: http://www.ema.europa.eu/docs/en_GB/document_library/EPAR—Product_Information/human/002455/WC500135055.pdf [Last accessed 10 Aug. 2017].
13. Younes A, Connors J M, Park S I, et al. Brentuximab vedotin combined with ABVD or AVD for patients with newly diagnosed Hodgkin's lymphoma: a phase 1, open-label, dose-escalation study. Lancet Oncol 2013; 14:1348-56.
14. Connors J M, Ansell S M, Fanale M, Park S I, Younes A. Five-year follow-up of brentuximab vedotin combined with ABVD or AVD for advanced stage classical Hodgkin lymphoma. Blood 2017.
15. Hasenclever D, Diehl V. A prognostic score for advanced Hodgkin's disease. International Prognostic Factors Project on Advanced Hodgkin's Disease. N Engl J Med 1998; 339:1506-14.
16. Meignan M, Gallamini A, Haioun C, Polliack A. Report on the Second International Workshop on interim positron emission tomography in lymphoma held in Menton, France, 8-9 Apr. 2010. Leuk Lymphoma 2010; 51:2171-80.
17. Fauci A S, Braunwauld E, Kasper D L, et al. Ann Arbor Staging System for Hodgkin's Disease. Harrison's Manual of Medicine. 17th ed. New York, N.Y.: McGraw-Hill; 2009.
18. Campo E, Swerdlow S H, Harris N L, Pileri S, Stein H, Jaffe E S. The 2008 WHO classification of lymphoid neoplasms and beyond: evolving concepts and practical applications. Blood 2011; 117:5019-32.
19. Oken M M, Creech R H, Tormey D C, et al. Toxicity and response criteria of the Eastern Cooperative Oncology Group. Am J Clin Oncol 1982; 5:649-55.
20. Cheson B D, Pfistner B, Juweid M E, et al. Revised response criteria for malignant lymphoma. J Clin Oncol 2007; 25:579-86.
21. Barnes J A, LaCasce A S, Zukotynski K, et al. End-of-treatment but not interim PET scan predicts outcome in nonbulky limited-stage Hodgkin's lymphoma. Ann Oncol 2011; 22:910-5.
22. Engert A, Haverkamp H, Kobe C, et al. Reduced-intensity chemotherapy and PET-guided radiotherapy in patients with advanced stage Hodgkin's lymphoma (HD15 trial): a randomised, open-label, phase 3 non-inferiority trial. Lancet 2012; 379:1791-9.
23. Spaepen K, Stroobants S, Dupont P, et al. Can positron emission tomography with [(18)F]-fluorodeoxyglucose after first-line treatment distinguish Hodgkin's disease patients who need additional therapy from others in whom additional therapy would mean avoidable toxicity? Br J Haematol 2001; 115:272-8.
24. Engert A, Ballova V, Haverkamp H, et al. Hodgkin's lymphoma in elderly patients: a comprehensive retrospective analysis from the German Hodgkin's Study Group. J Clin Oncol 2005; 23:5052-60.
25. Shenoy P, Maggioncalda A, Malik N, Flowers C R. Incidence patterns and outcomes for Hodgkin lymphoma patients in the United States. Adv Hematol 2011; 2011: 725219.
26. Matasar M J, Ford J S, Riedel E R, Salz T, Oeffinger K C, Straus D J. Late morbidity and mortality in patients with Hodgkin's lymphoma treated during adulthood. J Natl Cancer Inst 2015; 107.
27. Ng A K, van Leeuwen F E. Hodgkin lymphoma: Late effects of treatment and guidelines for surveillance. Semin Hematol 2016; 53:209-15.

What is claimed:

1. A method for treating a hematologic cancer in a subject comprising administering to the subject a therapy comprising an anti-CD30 antibody drug conjugate and prophylactically administering to the subject a granulopoiesis stimulating factor, wherein the granulopoiesis stimulating factor is administered beginning with cycle 1 of the administration of anti-CD30 antibody drug conjugate, wherein the antibody drug conjugate comprises monomethyl auristatin E and a protease-cleavable linker consisting of a thiolreactive maleimidocaproyl spacer, a valine-citrulline dipeptide, and a p-amino-benzyloxycarbonyl spacer.

2. The method of claim 1,
wherein the granulopoiesis stimulating factor is administered from 1 day to 7 days after beginning with cycle 1 of the administration of anti-CD30 antibody drug conjugate, or
wherein the granulopoiesis stimulating factor is administered from 2 days to 5 days after beginning with cycle 1 of the administration of anti-CD30 antibody drug conjugate.

3. The method of claim 1,
wherein the granulopoiesis stimulating factor is administered from 1 day to 7 days after a second or subsequent, administration of anti-CD30 antibody drug conjugate, or
wherein the granulopoiesis stimulating factor is administered from 2 days to 5 days after the a second or subsequent administration of anti-CD30 antibody drug conjugate.

4. The method of claim 1 wherein, the granulopoiesis stimulating factor is administered 24 hours to 36 hours after each administration of anti-CD30 antibody drug conjugate.

5. The method of claim 1 wherein the granulopoiesis stimulating factor is administered to a subject that has not received anti-CD30 antibody drug conjugate therapy previously.

6. The method of claim 1 wherein the subject has not experienced treatment-emergent grade 3-4 neutropenia after anti-CD30 antibody drug conjugate administration.

7. The method of claim 1 wherein the granulopoiesis stimulating factor is a granulocyte-colony stimulating factor (GCSF).

8. The method of claim 7 wherein the GCSF is a long-acting GCSF or a non long-acting GCSF.

9. The method of claim 7 wherein
i) the GCSF is long-acting GCSF, and is administered 1 day or 2 days after beginning with cycle 1 of the administration of anti-CD30 antibody drug conjugate; or
ii) the GCSF is not long acting, and is administered 1, 2, 3, 4, 5, 6 or 7 days after beginning with cycle 1 of the administration of anti-CD30 antibody drug conjugate.

10. The method of claim 9 wherein the G-CSF is administered 24 hours to 36 hours after each administration of anti-CD30 antibody drug conjugate.

11. The method of claim 1 wherein the anti-CD30 antibody drug conjugate is administered every 3 weeks.

12. The method of claim 1 wherein the anti-CD30 antibody drug conjugate is administered every 2 weeks, optionally on day 1 and day 15 of a 28-day cycle.

13. The method of claim 1 wherein the anti-CD30 antibody drug conjugate is administered for no more than six cycles.

14. The method of claim 1 further comprising administering a chemotherapy consisting essentially of doxorubicin, vinblastine, and dacarbazine (AVD) as a combination therapy.

15. The method of claim 1 wherein the anti-CD30 antibody of the anti-CD30 antibody drug conjugate comprises
  i) a heavy chain CDR1 set out in SEQ ID NO: 4, a heavy chain CDR2 set out in SEQ ID NO: 6, a heavy chain CDR3 set out in SEQ ID NO: 8; and
  ii) a light chain CDR1 set out in SEQ ID NO: 12, a light chain CDR2 set out in SEQ ID NO: 14, and a light chain CDR13 set out in SEQ ID NO: 16.

16. The method of claim 15 wherein the anti-CD30 antibody of the anti-CD30 antibody drug conjugate comprises
  i) an amino acid sequence at least 85% identical to a heavy chain variable region set out in SEQ ID NO: 2 and
  ii) an amino acid sequence at least 85% identical to a light chain variable region set out in SEQ ID NO: 10.

17. The method of claim 1 wherein the anti-CD30 antibody of the anti-CD30 antibody drug conjugate is a monoclonal anti-CD30 antibody or a chimeric AC10 antibody.

18. The method of claim 1 wherein the anti-CD30 antibody drug conjugate is brentuximab vedotin.

19. The method of claim 1 wherein the granulopoiesis stimulating factor is administered in a dose range from 5 to 10 μg/kg/day, or 300 to 600 μg/day, or 6 mg/dose.

20. The method of claim 1 wherein the granulopoiesis stimulating factor is given intravenously or subcutaneously.

* * * * *

UNITED STATES PATENT AND TRADEMARK OFFICE
CERTIFICATE OF CORRECTION

PATENT NO. : 11,795,229 B2
APPLICATION NO. : 16/755403
DATED : October 24, 2023
INVENTOR(S) : Thomas Manley et al.

It is certified that error appears in the above-identified patent and that said Letters Patent is hereby corrected as shown below:

In the Claims

At Column 39, Line 43, "thiolreactive" should be -- thiol-reactive --.

At Column 39, Line 61, "the a" should be -- a --.

At Column 40, Line 45, "wherein" should be -- wherein, --.

At Column 41, Line 2, "comprises" should be -- comprises: --.

At Column 41, Lines 10-11, "comprises" should be -- comprises: --.

At Column 41, Line 13, "NO: 2" should be -- NO: 2; --.

Signed and Sealed this
Fifteenth Day of July, 2025

Coke Morgan Stewart
*Acting Director of the United States Patent and Trademark Office*

SEQUENCE LISTING

<160> NUMBER OF SEQ ID NOS: 16

<210> SEQ ID NO 1
<211> LENGTH: 351
<212> TYPE: DNA
<213> ORGANISM: Mus musculus
<220> FEATURE:
<221> NAME/KEY: CDS
<222> LOCATION: (1)..(351)

<400> SEQUENCE: 1

```
cag atc cag ctg cag cag tct gga cct gag gtg gtg aag cct ggg gct      48
Gln Ile Gln Leu Gln Gln Ser Gly Pro Glu Val Val Lys Pro Gly Ala
1               5                   10                  15 tca gtg aag ata tcc tgc aag gct tct ggc tac acc ttc act gac tac      96
Ser Val Lys Ile Ser Cys Lys Ala Ser Gly Tyr Thr Phe Thr Asp Tyr
            20                  25                  30 tat ata acc tgg gtg aag cag aag cct gga cag gga ctt gag tgg att     144
Tyr Ile Thr Trp Val Lys Gln Lys Pro Gly Gln Gly Leu Glu Trp Ile
        35                  40                  45 gga tgg att tat cct gga agc ggt aat act aag tac aat gag aag ttc     192
Gly Trp Ile Tyr Pro Gly Ser Gly Asn Thr Lys Tyr Asn Glu Lys Phe
    50                  55                  60 aag ggc aag gcc aca ttg act gta gac aca tcc tcc agc aca gcc ttc     240
Lys Gly Lys Ala Thr Leu Thr Val Asp Thr Ser Ser Ser Thr Ala Phe
65                  70                  75                  80 atg cag ctc agc agc ctg aca tct gag gac act gct gtc tat ttc tgt     288
Met Gln Leu Ser Ser Leu Thr Ser Glu Asp Thr Ala Val Tyr Phe Cys
                85                  90                  95 gcg aac tat ggt aac tac tgg ttt gct tac tgg ggc caa ggg act cag     336
Ala Asn Tyr Gly Asn Tyr Trp Phe Ala Tyr Trp Gly Gln Gly Thr Gln
            100                 105                 110 gtc act gtc tct gca                                                 351
Val Thr Val Ser Ala
        115
```

<210> SEQ ID NO 2
<211> LENGTH: 117
<212> TYPE: PRT
<213> ORGANISM: Mus musculus

<400> SEQUENCE: 2

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115
```

<210> SEQ ID NO 3

```
<211> LENGTH: 15
<212> TYPE: DNA
<213> ORGANISM: Mus musculus

<400> SEQUENCE: 3
gactactata taacc                                                      15

<210> SEQ ID NO 4
<211> LENGTH: 5
<212> TYPE: PRT
<213> ORGANISM: Mus musculus

<400> SEQUENCE: 4

Asp Tyr Tyr Ile Thr
1               5

<210> SEQ ID NO 5
<211> LENGTH: 51
<212> TYPE: DNA
<213> ORGANISM: Mus musculus

<400> SEQUENCE: 5
tggatttatc ctggaagcgg taatactaag tacaatgaga agttcaaggg c              51

<210> SEQ ID NO 6
<211> LENGTH: 17
<212> TYPE: PRT
<213> ORGANISM: Mus musculus

<400> SEQUENCE: 6

Trp Ile Tyr Pro Gly Ser Gly Asn Thr Lys Tyr Asn Glu Lys Phe Lys
1               5                   10                  15

Gly

<210> SEQ ID NO 7
<211> LENGTH: 24
<212> TYPE: DNA
<213> ORGANISM: Mus musculus

<400> SEQUENCE: 7
tatggtaact actggtttgc ttac                                            24

<210> SEQ ID NO 8
<211> LENGTH: 8
<212> TYPE: PRT
<213> ORGANISM: Mus musculus

<400> SEQUENCE: 8

Tyr Gly Asn Tyr Trp Phe Ala Tyr
1               5

<210> SEQ ID NO 9
<211> LENGTH: 333
<212> TYPE: DNA
<213> ORGANISM: Mus musculus
<220> FEATURE:
<221> NAME/KEY: CDS
<222> LOCATION: (1)..(333)

<400> SEQUENCE: 9 gac att gtg ctg acc caa tct cca gct tct ttg gct gtg tct cta ggg      48
Asp Ile Val Leu Thr Gln Ser Pro Ala Ser Leu Ala Val Ser Leu Gly
1               5                   10                  15 cag agg gcc acc atc tcc tgc aag gcc agc caa agt gtt gat ttt gat      96
```

```
                Gln Arg Ala Thr Ile Ser Cys Lys Ala Ser Gln Ser Val Asp Phe Asp
                                20                  25                  30 ggt gat agt tat atg aac tgg tac caa cag aaa cca gga cag cca ccc        144
Gly Asp Ser Tyr Met Asn Trp Tyr Gln Gln Lys Pro Gly Gln Pro Pro
         35                  40                  45 aaa gtc ctc atc tat gct gca tcc aat cta gaa tct ggg atc cca gcc        192
Lys Val Leu Ile Tyr Ala Ala Ser Asn Leu Glu Ser Gly Ile Pro Ala
 50                  55                  60 agg ttt agt ggc agt ggg tct ggg aca gac ttc acc ctc aac atc cat        240
Arg Phe Ser Gly Ser Gly Ser Gly Thr Asp Phe Thr Leu Asn Ile His
 65                  70                  75                  80 cct gtg gag gag gag gat gct gca acc tat tac tgt cag caa agt aat        288
Pro Val Glu Glu Glu Asp Ala Ala Thr Tyr Tyr Cys Gln Gln Ser Asn
                 85                  90                  95 gag gat ccg tgg acg ttc ggt gga ggc acc aag ctg gaa atc aaa            333
Glu Asp Pro Trp Thr Phe Gly Gly Gly Thr Lys Leu Glu Ile Lys
            100                 105                 110
```

```
<210> SEQ ID NO 10
<211> LENGTH: 111
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
                20                  25                  30

Gly Asp Ser Tyr Met Asn Trp Tyr Gln Gln Lys Pro Gly Gln Pro Pro
         35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Trp Thr Phe Gly Gly Gly Thr Lys Leu Glu Ile Lys
            100                 105                 110
```

```
<210> SEQ ID NO 11
<211> LENGTH: 45
<212> TYPE: DNA
<213> ORGANISM: Mus musculus

<400> SEQUENCE: 11
aaggccagcc aaagtgttga ttttgatggt gatagttata tgaac                      45
```

```
<210> SEQ ID NO 12
<211> LENGTH: 15
<212> TYPE: PRT
<213> ORGANISM: Mus musculus

<400> SEQUENCE: 12

Lys Ala Ser Gln Ser Val Asp Phe Asp Gly Asp Ser Tyr Met Asn
1               5                   10                  15
```

```
<210> SEQ ID NO 13
<211> LENGTH: 21
<212> TYPE: DNA
<213> ORGANISM: Mus musculus
```

```
<400> SEQUENCE: 13
gctgcatcca atctagaatc t                                              21

<210> SEQ ID NO 14
<211> LENGTH: 7
<212> TYPE: PRT
<213> ORGANISM: Mus musculus

<400> SEQUENCE: 14

Ala Ala Ser Asn Leu Glu Ser
1               5

<210> SEQ ID NO 15
<211> LENGTH: 27
<212> TYPE: DNA
<213> ORGANISM: Mus musculus

<400> SEQUENCE: 15
cagcaaagta atgaggatcc gtggacg                                        27

<210> SEQ ID NO 16
<211> LENGTH: 9
<212> TYPE: PRT
<213> ORGANISM: Mus musculus

<400> SEQUENCE: 16

Gln Gln Ser Asn Glu Asp Pro Trp Thr
1               5
```